(12) United States Patent
Swanick et al.

(10) Patent No.: US 11,083,823 B2
(45) Date of Patent: *Aug. 10, 2021

(54) TISSUE-SEPARATING FATTY ACID ADHESION BARRIER

(71) Applicant: ATRIUM MEDICAL CORPORATION, Merrimack, NH (US)

(72) Inventors: Thomas M. Swanick, Hillsborough, NH (US); Joe Bienkiewicz, Westford, MA (US); Joseph Ferraro, Londonderry, NH (US); Paul Martakos, Pelham, NH (US); Keith M. Faucher, Milford, NH (US); Alicia Dale, Hudson, NH (US)

(73) Assignee: ATRIUM MEDICAL CORPORATION, Merrimack, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,018

(22) Filed: Nov. 17, 2017

(65) Prior Publication Data

US 2018/0133376 A1    May 17, 2018

Related U.S. Application Data

(60) Division of application No. 15/001,585, filed on Jan. 20, 2016, now Pat. No. 9,844,611, which is a division of application No. 12/581,582, filed on Oct. 19, 2009, now Pat. No. 9,278,161, which is a continuation of application No. 12/401,243, filed on Mar. 10, 2009, now Pat. No. 9,427,423, which is a continuation-in-part of application No. 11/978,840, filed on Oct. 30, 2007, now Pat. No. 8,574,627, which is a continuation-in-part of application No. 11/237,420, filed on Sep. 28, 2005, now Pat. No. 9,801,913, which is a continuation-in-part of application No. 11/237,264, filed on Sep. 28, 2005, now Pat. No. 8,795,703.

(51) Int. Cl.
| | |
|---|---|
| A61L 31/14 | (2006.01) |
| A61L 31/10 | (2006.01) |
| A61K 9/10 | (2006.01) |
| A61L 31/00 | (2006.01) |
| A61F 2/06 | (2013.01) |

(52) U.S. Cl.
CPC .............. *A61L 31/148* (2013.01); *A61K 9/10* (2013.01); *A61L 31/00* (2013.01); *A61L 31/10* (2013.01); *A61L 31/145* (2013.01); *A61F 2/06* (2013.01); *A61F 2250/0067* (2013.01); *A61L 2420/02* (2013.01)

(58) Field of Classification Search
None
See application file for complete search history.

(56) References Cited

U.S. PATENT DOCUMENTS

| | | | |
|---|---|---|---|
| 1,948,959 A * | 2/1934 | Croce | 106/222 |
| 2,368,306 A | 1/1945 | Kiefer et al. | |
| 2,403,458 A | 7/1946 | Ransom | |
| 2,555,976 A | 6/1951 | Keenan | |
| 2,735,814 A | 2/1956 | Hodson et al. | C10M 173/00 106/38.24 |
| 2,986,540 A | 5/1961 | Posnansky | |
| 3,328,259 A * | 6/1967 | Anderson | A61L 15/28 424/404 |
| 3,464,413 A | 9/1969 | Goldfarb et al. | |
| 3,556,294 A | 1/1971 | Walck, III | |
| 3,567,820 A | 3/1971 | Sperti | |
| 3,803,109 A | 4/1974 | Nemoto | |
| 3,967,728 A | 7/1976 | Gordon et al. | |
| 4,185,637 A | 1/1980 | Mattei | |
| 4,308,120 A | 12/1981 | Pennewiss et al. | |
| 4,323,547 A | 4/1982 | Knust et al. | |
| 4,345,414 A | 8/1982 | Bornat et al. | |
| 4,447,418 A | 5/1984 | Maddoux | |
| 4,557,925 A | 12/1985 | Lindahl et al. | |
| 4,655,221 A | 4/1987 | Devereux | |
| 4,664,114 A | 5/1987 | Ghodsian | |
| 4,702,252 A | 10/1987 | Brooks et al. | |
| 4,711,902 A | 12/1987 | Serno | |

(Continued)

FOREIGN PATENT DOCUMENTS

| | | |
|---|---|---|
| CN | 1360951 A | 7/2002 |
| CN | 1429559 A | 7/2003 |

(Continued)

OTHER PUBLICATIONS

Garg et al. Lipids 1988 23:847-852 (Year: 1988).*
Benchabane et al. Colloid and Polymer Science 2008 286:1173-1180 (Year: 2008).*
Examination Report issued in counterpart Indian Application No. 3605/DELNP/2012, dated Mar. 23, 2018.
Final Office Action dated Mar. 30, 2017 for related U.S. Appl. No. 11/237,420, 20 pages.
Henderson, R. James et al., "Hydrolysis of Fish Oils Containing Polymers of Triacylglycerols by Pancreatic Lipase in vitro", LIPIDS, vol. 28, No. 4, 1993, pp. 313-319.
Oxford Reference, A Dictionary of Chemistry, 6th edition, John Daintith, 2008, 3 pages.

(Continued)

*Primary Examiner* — Robert A Wax
*Assistant Examiner* — Caralynne E Helm
(74) *Attorney, Agent, or Firm* — Wesley Scott Ashton

(57) ABSTRACT

Exemplary embodiments of the present invention provide adhesion barriers having anti-adhesion and tissue fixating properties. The adhesion barriers are formed of fatty acid based films. The fatty acid-based films may be formed from fatty acid-derived biomaterials. The films may be coated with, or may include, tissue fixating materials to create the adhesion barrier. The adhesion barriers are well tolerated by the body, have anti-inflammation properties, fixate, well to tissue, and have a residence time sufficient to prevent post-surgical adhesions.

4 Claims, 7 Drawing Sheets

(56) References Cited

U.S. PATENT DOCUMENTS

| | | |
|---|---|---|
| 4,733,665 A | 3/1988 | Palmaz |
| 4,769,038 A | 9/1988 | Bendavid et al. |
| 4,813,210 A | 3/1989 | Masuda et al. |
| 4,814,329 A | 3/1989 | Harsanyi et al. |
| 4,824,436 A | 4/1989 | Wolinsky |
| 4,846,844 A | 7/1989 | De Leon et al. |
| 4,847,301 A | 7/1989 | Murray |
| 4,880,455 A | 11/1989 | Blank |
| 4,883,667 A | 11/1989 | Eckenhoff |
| 4,886,787 A | 12/1989 | de Belder et al. |
| 4,894,231 A | 1/1990 | Moreau et al. |
| 4,895,724 A | 1/1990 | Cardinal et al. |
| 4,911,707 A | 3/1990 | Heiber et al. |
| 4,937,254 A | 6/1990 | Sheffield et al. |
| 4,938,763 A | 7/1990 | Dunn et al. |
| 4,941,308 A | 7/1990 | Grabenkort et al. |
| 4,941,877 A | 7/1990 | Montano, Jr. |
| 4,947,840 A | 8/1990 | Yannas et al. |
| 4,952,419 A | 8/1990 | De Leon et al. |
| 4,968,302 A | 11/1990 | Schluter et al. |
| 4,994,033 A | 2/1991 | Shockey et al. |
| 5,017,229 A | 5/1991 | Burns et al. |
| 5,041,125 A | 8/1991 | Montano, Jr. |
| 5,049,132 A | 9/1991 | Shaffer et al. |
| 5,061,281 A | 10/1991 | Mares et al. |
| 5,071,609 A | 12/1991 | Tu et al. |
| 5,087,244 A | 2/1992 | Wolinsky et al. |
| 5,087,246 A | 2/1992 | Smith |
| 5,102,402 A | 4/1992 | Dror et al. |
| 5,118,493 A | 6/1992 | Kelley et al. |
| 5,132,115 A | 7/1992 | Wolter et al. |
| 5,147,374 A | 9/1992 | Fernandez |
| 5,151,272 A | 9/1992 | Engstrom et al. |
| 5,171,148 A | 12/1992 | Wasserman et al. |
| 5,176,956 A | 1/1993 | Jevne et al. |
| 5,179,174 A | 1/1993 | Elton |
| 5,199,951 A | 4/1993 | Spears |
| 5,202,310 A | 4/1993 | Levy et al. |
| 5,206,077 A | 4/1993 | Cowley et al. |
| 5,254,105 A | 10/1993 | Haaga |
| 5,267,985 A | 12/1993 | Shimada et al. |
| 5,279,565 A | 1/1994 | Klein et al. |
| 5,282,785 A | 2/1994 | Shapland et al. |
| 5,283,257 A | 2/1994 | Gregory et al. |
| 5,286,254 A | 2/1994 | Shapland et al. |
| 5,295,962 A | 3/1994 | Crocker et al. |
| 5,304,121 A | 4/1994 | Sahatjian |
| 5,336,178 A | 8/1994 | Kaplan et al. |
| 5,356,432 A | 10/1994 | Rutkow et al. |
| 5,368,602 A | 11/1994 | de la Torre |
| 5,371,109 A | 12/1994 | Engstrom et al. |
| 5,380,328 A | 1/1995 | Morgan |
| 5,387,658 A | 2/1995 | Schroder et al. |
| 5,403,283 A | 4/1995 | Luther |
| 5,411,951 A | 5/1995 | Mitchell |
| 5,411,988 A | 6/1995 | Bochow et al. |
| 5,447,940 A | 9/1995 | Harvey et al. |
| 5,456,666 A | 10/1995 | Campbell et al. |
| 5,456,720 A | 10/1995 | Schultz et al. |
| 5,458,568 A | 10/1995 | Racchini et al. |
| 5,458,572 A | 10/1995 | Campbell et al. |
| 5,464,650 A | 11/1995 | Berg et al. |
| 5,468,242 A | 11/1995 | Reisberg |
| 5,480,436 A * | 1/1996 | Bakker .................. A61L 31/06 600/37 |
| 5,480,653 A | 1/1996 | Aguadisch ........... A61K 9/2036 424/425 |
| 5,490,839 A | 2/1996 | Wang et al. |
| 5,498,238 A | 3/1996 | Shapland et al. |
| 5,499,971 A | 3/1996 | Shapland et al. |
| 5,509,899 A | 4/1996 | Fan et al. |
| 5,514,092 A | 5/1996 | Forman et al. |
| 5,547,677 A | 8/1996 | Wright |
| 5,549,901 A | 8/1996 | Wright |
| 5,558,071 A | 9/1996 | Ward et al. |
| 5,569,198 A | 10/1996 | Racchini |
| 5,573,781 A | 11/1996 | Brown et al. |
| 5,579,149 A | 11/1996 | Moret et al. |
| 5,580,923 A | 12/1996 | Yeung et al. |
| 5,589,508 A | 12/1996 | Schlotzer et al. |
| 5,591,230 A | 1/1997 | Horn et al. |
| 5,593,441 A | 1/1997 | Lichtenstein et al. |
| 5,603,721 A | 2/1997 | Lau et al. |
| 5,605,696 A | 2/1997 | Eury et al. |
| 5,612,074 A | 3/1997 | Leach |
| 5,614,284 A | 3/1997 | Kranzler et al. |
| 5,627,077 A | 5/1997 | Dyllick-Brenzinger et al. |
| 5,628,730 A | 5/1997 | Shapland et al. |
| 5,629,021 A | 5/1997 | Wright |
| 5,634,899 A | 6/1997 | Shapland et al. |
| 5,634,931 A * | 6/1997 | Kugel .................. A61F 2/0063 606/1 |
| 5,637,113 A | 6/1997 | Tartaglia et al. |
| 5,637,317 A | 6/1997 | Dietl |
| 5,641,767 A | 6/1997 | Wess et al. |
| 5,665,115 A | 9/1997 | Cragg |
| 5,693,014 A | 12/1997 | Abele et al. |
| 5,695,525 A | 12/1997 | Mulhauser et al. |
| 5,700,286 A | 12/1997 | Tartaglia et al. |
| 5,700,848 A | 12/1997 | Soon-Shiong et al. |
| 5,705,485 A * | 1/1998 | Cini .................. A61K 9/0014 514/8.2 |
| 5,731,346 A | 3/1998 | Egberg et al. |
| 5,736,152 A | 4/1998 | Dunn |
| 5,738,869 A | 4/1998 | Fischer et al. |
| 5,747,533 A | 5/1998 | Egberg et al. |
| 5,749,845 A | 5/1998 | Hildebrand et al. |
| 5,753,259 A | 5/1998 | Engstrom et al. |
| 5,760,081 A | 6/1998 | Leaf et al. |
| 5,766,246 A | 6/1998 | Mulhausser et al. |
| 5,766,710 A | 6/1998 | Turnlund et al. |
| 5,789,465 A | 8/1998 | Harvey et al. |
| 5,800,392 A | 9/1998 | Racchini |
| 5,807,306 A | 9/1998 | Shapland et al. |
| 5,817,343 A | 10/1998 | Burke |
| 5,824,082 A | 10/1998 | Brown |
| 5,827,325 A | 10/1998 | Landgrebe et al. |
| 5,828,785 A | 10/1998 | Kitsuki |
| 5,837,313 A | 11/1998 | Ding et al. |
| 5,843,172 A | 12/1998 | Yan |
| 5,843,919 A | 12/1998 | Burger |
| 5,865,787 A | 2/1999 | Shapland et al. |
| 5,874,470 A | 2/1999 | Nehne et al. |
| 5,879,359 A | 3/1999 | Dorigatti et al. |
| 5,897,911 A | 4/1999 | Loeffler |
| 5,898,040 A | 4/1999 | Shalaby et al. |
| 5,902,266 A | 5/1999 | Leone et al. |
| 5,906,831 A | 5/1999 | Larsson et al. |
| 5,931,165 A | 8/1999 | Reich et al. |
| 5,947,977 A | 9/1999 | Slepian et al. |
| 5,954,767 A | 9/1999 | Pajotin et al. |
| 5,955,502 A | 9/1999 | Hansen et al. |
| 5,986,043 A | 11/1999 | Hubbell et al. |
| 6,004,549 A | 12/1999 | Reichert et al. |
| 6,005,004 A | 12/1999 | Katz et al. |
| 6,010,480 A | 1/2000 | Abele et al. |
| 6,010,766 A | 1/2000 | Braun et al. |
| 6,010,776 A | 1/2000 | Exsted et al. |
| 6,013,055 A | 1/2000 | Bampos et al. |
| 6,015,844 A | 1/2000 | Harvey et al. |
| 6,028,164 A | 2/2000 | Loomis |
| 6,033,380 A | 3/2000 | Butaric et al. |
| 6,033,436 A | 3/2000 | Steinke et al. |
| 6,040,330 A | 3/2000 | Hausheer et al. |
| 6,048,332 A | 4/2000 | Duffy et al. |
| 6,048,725 A | 4/2000 | Shimada et al. |
| 6,056,970 A | 5/2000 | Greenawalt et al. |
| 6,066,777 A | 5/2000 | Benchetrit |
| 6,075,180 A | 6/2000 | Sharber et al. |
| 6,077,698 A | 6/2000 | Swan et al. |
| 6,080,442 A | 6/2000 | Yoshikawa et al. |
| 6,083,950 A | 7/2000 | Anand et al. |
| 6,090,809 A | 7/2000 | Anand et al. |
| 6,093,792 A | 7/2000 | Gross et al. |

(56) References Cited

U.S. PATENT DOCUMENTS

| | | | |
|---|---|---|---|
| 6,117,911 A | 9/2000 | Grainger et al. |
| 6,120,477 A | 9/2000 | Campbell et al. |
| 6,120,539 A | 9/2000 | Eldridge et al. |
| 6,120,789 A | 9/2000 | Dunn |
| 6,132,765 A | 10/2000 | DiCosmo et al. |
| 6,146,358 A | 11/2000 | Rowe |
| 6,152,944 A | 11/2000 | Holman et al. |
| 6,176,863 B1 | 1/2001 | Kugel et al. |
| 6,193,746 B1 | 2/2001 | Strecker |
| 6,197,357 B1 | 3/2001 | Lawton et al. |
| 6,200,985 B1 | 3/2001 | Cottens et al. |
| 6,203,551 B1 | 3/2001 | Wu |
| 6,206,916 B1 | 3/2001 | Furst |
| 6,211,315 B1 | 4/2001 | Larock et al. |
| 6,224,579 B1 | 5/2001 | Modak et al. |
| 6,224,909 B1 | 5/2001 | Opitz et al. |
| 6,228,383 B1 | 5/2001 | Hansen et al. |
| 6,229,032 B1 | 5/2001 | Jacobs et al. |
| 6,231,600 B1 | 5/2001 | Zhong |
| 6,245,366 B1 | 6/2001 | Popplewell et al. |
| 6,245,811 B1 | 6/2001 | Horrobin et al. |
| 6,254,634 B1 | 7/2001 | Anderson et al. |
| 6,258,124 B1 | 7/2001 | Darois et al. |
| 6,262,109 B1 | 7/2001 | Clark et al. |
| 6,273,913 B1 | 8/2001 | Wright et al. |
| 6,284,268 B1 | 9/2001 | Mishra et al. |
| 6,287,285 B1 | 9/2001 | Michal et al. |
| 6,287,316 B1 | 9/2001 | Agarwal et al. |
| 6,299,604 B1 | 10/2001 | Ragheb et al. |
| 6,306,438 B1 | 10/2001 | Oshlack et al. |
| 6,326,072 B1 | 12/2001 | Ojeda et al. |
| 6,326,360 B1 | 12/2001 | Kanazawa et al. |
| 6,331,568 B1 | 12/2001 | Horrobin |
| 6,342,254 B1 | 1/2002 | Soudant et al. |
| 6,346,110 B2 | 2/2002 | Wu |
| 6,355,063 B1 | 3/2002 | Calcote |
| 6,358,556 B1 | 3/2002 | Ding et al. |
| 6,364,856 B1 | 4/2002 | Ding et al. |
| 6,364,893 B1 | 4/2002 | Sahatjian et al. |
| 6,364,903 B2 | 4/2002 | Tseng et al. |
| 6,368,541 B1 | 4/2002 | Pajotin et al. |
| 6,368,658 B1 | 4/2002 | Schwarz et al. |
| 6,369,039 B1 | 4/2002 | Palasis et al. |
| 6,387,301 B1 | 5/2002 | Nakajima et al. |
| 6,387,379 B1 | 5/2002 | Goldberg et al. |
| 6,410,587 B1 | 6/2002 | Grainger et al. |
| 6,444,318 B1 | 9/2002 | Guire et al. |
| 6,451,373 B1 | 9/2002 | Hossainy et al. |
| 6,463,323 B1 | 10/2002 | Conrad-Vlasak et al. |
| 6,465,525 B1 | 10/2002 | Guire et al. |
| 6,471,980 B2 | 10/2002 | Sirhan et al. |
| 6,479,683 B1 | 11/2002 | Abney et al. |
| 6,485,752 B1 | 11/2002 | Rein et al. |
| 6,491,938 B2 | 12/2002 | Kunz et al. |
| 6,500,174 B1 | 12/2002 | Maguire et al. |
| 6,500,453 B2 | 12/2002 | Brey et al. |
| 6,503,556 B2 | 1/2003 | Harish et al. |
| 6,506,410 B1 * | 1/2003 | Park ............... A61K 9/1635 424/489 |
| 6,525,145 B2 | 2/2003 | Gevaert et al. |
| 6,527,801 B1 | 3/2003 | Dutta |
| 6,534,693 B2 | 3/2003 | Fischell et al. |
| 6,541,116 B2 | 4/2003 | Michal et al. |
| 6,544,223 B1 | 4/2003 | Kokish |
| 6,544,224 B1 | 4/2003 | Steese-Bradley |
| 6,548,081 B2 * | 4/2003 | Sadozai ............... A61L 31/10 424/426 |
| 6,565,659 B1 | 5/2003 | Pacetti et al. |
| 6,569,441 B2 | 5/2003 | Kunz et al. |
| 6,579,851 B2 | 6/2003 | Gocke et al. |
| 6,596,002 B2 | 7/2003 | Therin et al. |
| 6,599,323 B2 | 7/2003 | Melican et al. |
| 6,610,006 B1 | 8/2003 | Amid et al. |
| 6,610,035 B2 | 8/2003 | Yang et al. |
| 6,610,068 B1 | 8/2003 | Yang |
| 6,616,650 B1 | 9/2003 | Rowe |
| 6,630,151 B1 | 10/2003 | Tarletsky et al. |
| 6,630,167 B2 | 10/2003 | Zhang |
| 6,632,822 B1 | 10/2003 | Rickards et al. |
| 6,641,611 B2 | 11/2003 | Jayaraman |
| 6,645,547 B1 | 11/2003 | Shekalim et al. |
| 6,663,880 B1 | 12/2003 | Roorda et al. |
| 6,669,735 B1 | 12/2003 | Pelissier |
| 6,670,355 B2 | 12/2003 | Azrolan et al. |
| 6,677,342 B2 | 1/2004 | Wolff et al. |
| 6,677,386 B1 | 1/2004 | Giezen et al. |
| 6,685,956 B2 | 2/2004 | Chu et al. |
| 6,689,388 B2 | 2/2004 | Kuhrts |
| 6,696,583 B2 | 2/2004 | Koncar et al. |
| 6,723,133 B1 | 4/2004 | Pajotin |
| 6,730,016 B1 | 5/2004 | Cox et al. |
| 6,730,064 B2 | 5/2004 | Ragheb et al. |
| 6,740,122 B1 | 5/2004 | Pajotin |
| 6,753,071 B1 | 6/2004 | Pacetti |
| 6,758,847 B2 | 7/2004 | Maguire |
| 6,761,903 B2 | 7/2004 | Chen et al. |
| 6,764,509 B2 | 7/2004 | Chinn et al. |
| 6,776,796 B2 | 8/2004 | Falotico et al. |
| 6,794,485 B2 | 9/2004 | Shalaby et al. |
| 6,808,536 B2 | 10/2004 | Wright et al. |
| 6,833,004 B2 | 12/2004 | Ishii et al. |
| 6,852,330 B2 | 2/2005 | Bowman et al. |
| 6,875,230 B1 | 4/2005 | Morita et al. |
| 6,884,428 B2 | 4/2005 | Binette et al. |
| 6,887,270 B2 | 5/2005 | Miller et al. |
| 6,899,729 B1 | 5/2005 | Cox et al. |
| 6,902,522 B1 | 6/2005 | Walsh et al. |
| 6,918,927 B2 | 7/2005 | Bates et al. |
| 6,996,952 B2 | 2/2006 | Gupta et al. |
| 7,070,858 B2 | 7/2006 | Shalaby et al. |
| 7,090,655 B2 | 8/2006 | Barry |
| 7,101,381 B2 | 9/2006 | Ford et al. |
| 7,112,209 B2 | 9/2006 | Ramshaw et al. |
| 7,135,164 B2 | 11/2006 | Rojanapanthu et al. |
| 7,152,611 B2 | 12/2006 | Brown et al. |
| 7,311,980 B1 | 12/2007 | Hossainy et al. |
| 7,323,178 B1 | 1/2008 | Zhang et al. |
| 7,323,189 B2 | 1/2008 | Pathak |
| 7,415,811 B2 | 8/2008 | Gottlieb et al. |
| 7,691,946 B2 | 4/2010 | Liu et al. |
| 7,854,958 B2 | 12/2010 | Kramer |
| 7,947,015 B2 | 5/2011 | Herweck et al. |
| 8,001,922 B2 | 8/2011 | Labrecque et al. |
| 8,021,331 B2 | 9/2011 | Herweck et al. |
| 8,124,127 B2 | 2/2012 | Faucher et al. |
| 8,298,290 B2 | 10/2012 | Pelissier et al. |
| 8,308,684 B2 | 11/2012 | Herweck et al. |
| 8,312,836 B2 | 11/2012 | Corbeil et al. |
| 8,461,129 B2 | 6/2013 | Boldue et al. |
| 8,501,229 B2 | 8/2013 | Faucher et al. |
| 8,722,077 B2 | 5/2014 | Labrecque et al. |
| 8,888,887 B2 | 11/2014 | Hargrove et al. |
| 9,000,040 B2 | 4/2015 | Faucher et al. |
| 9,012,506 B2 | 4/2015 | Faucher et al. |
| 9,220,820 B2 | 12/2015 | Faucher et al. |
| 9,278,161 B2 | 3/2016 | Swanick et al. |
| 9,427,423 B2 | 8/2016 | Swanick et al. |
| 9,493,636 B2 | 11/2016 | Ah et al. |
| 2001/0022988 A1 | 9/2001 | Schwarz et al. |
| 2001/0025034 A1 | 9/2001 | Arbiser |
| 2001/0025196 A1 | 9/2001 | Chinn et al. |
| 2001/0026803 A1 | 10/2001 | Tebbe et al. |
| 2001/0027299 A1 | 10/2001 | Yang et al. |
| 2001/0051595 A1 | 12/2001 | Lyons et al. |
| 2002/0002154 A1 | 1/2002 | Guivarct et al. |
| 2002/0007209 A1 | 1/2002 | Scheerder et al. |
| 2002/0012741 A1 | 1/2002 | Heinz et al. |
| 2002/0013590 A1 | 1/2002 | Therin et al. |
| 2002/0015970 A1 | 2/2002 | Murray et al. |
| 2002/0022052 A1 | 2/2002 | Dransfield |
| 2002/0026899 A1 | 3/2002 | McLaughlin et al. |
| 2002/0026900 A1 | 3/2002 | Huang et al. |
| 2002/0032414 A1 | 3/2002 | Ragherb et al. |
| 2002/0055701 A1 | 5/2002 | Fischell et al. |

(56) References Cited

U.S. PATENT DOCUMENTS

| | | |
|---|---|---|
| 2002/0077652 A1 | 6/2002 | Kieturakis et al. |
| 2002/0082679 A1 | 6/2002 | Sirhan et al. |
| 2002/0098278 A1 | 7/2002 | Bates et al. |
| 2002/0103494 A1 | 8/2002 | Pacey |
| 2002/0116045 A1 | 8/2002 | Eidenschink |
| 2002/0120333 A1 | 8/2002 | Keogh et al. |
| 2002/0122877 A1 | 9/2002 | Harish et al. |
| 2002/0127327 A1 | 9/2002 | Schwarz et al. |
| 2002/0142089 A1 | 10/2002 | Koike et al. |
| 2002/0183716 A1 | 12/2002 | Herweck et al. |
| 2002/0192352 A1 | 12/2002 | Dar |
| 2002/0193829 A1 | 12/2002 | Kennedy et al. |
| 2003/0003125 A1 | 1/2003 | Nathan et al. |
| 2003/0003221 A1 | 1/2003 | Zhong et al. |
| 2003/0004564 A1 | 1/2003 | Elkins et al. |
| 2003/0009213 A1 | 1/2003 | Yang |
| 2003/0033004 A1 | 2/2003 | Ishii et al. |
| 2003/0036803 A1 | 2/2003 | McGhan |
| 2003/0055403 A1 | 3/2003 | Nestenborg et al. |
| 2003/0065292 A1 | 4/2003 | Darouiche et al. |
| 2003/0065345 A1 | 4/2003 | Weadock |
| 2003/0069632 A1 | 4/2003 | De Scheerder et al. |
| 2003/0072784 A1 | 4/2003 | Williams |
| 2003/0077272 A1 | 4/2003 | Pathak |
| 2003/0077310 A1 | 4/2003 | Pathak et al. |
| 2003/0077452 A1 | 4/2003 | Guire et al. |
| 2003/0083740 A1 | 5/2003 | Pathak |
| 2003/0086958 A1 | 5/2003 | Arnold et al. |
| 2003/0094728 A1 | 5/2003 | Tayebi |
| 2003/0100955 A1* | 5/2003 | Greenawalt ............ A61L 27/48 623/23.74 |
| 2003/0108588 A1 | 6/2003 | Chen et al. |
| 2003/0124087 A1 | 7/2003 | Kim et al. |
| 2003/0130206 A1 | 7/2003 | Koziak et al. |
| 2003/0152609 A1 | 8/2003 | Fischell et al. |
| 2003/0175408 A1 | 9/2003 | Timm et al. |
| 2003/0176915 A1 | 9/2003 | Wright et al. |
| 2003/0181975 A1 | 9/2003 | Ishii et al. |
| 2003/0181988 A1 | 9/2003 | Rousseau |
| 2003/0187516 A1 | 10/2003 | Amid et al. |
| 2003/0191179 A1 | 10/2003 | Joshi-Hangal et al. |
| 2003/0204168 A1 | 10/2003 | Bosma et al. |
| 2003/0204618 A1 | 10/2003 | Foster et al. |
| 2003/0207019 A1 | 11/2003 | Shekalim et al. |
| 2003/0211230 A1 | 11/2003 | Pacetti et al. |
| 2003/0212462 A1 | 11/2003 | Gryska et al. |
| 2003/0220297 A1 | 11/2003 | Berstein et al. |
| 2004/0006296 A1 | 1/2004 | Fischell et al. |
| 2004/0013704 A1 | 1/2004 | Kabra et al. |
| 2004/0014810 A1 | 1/2004 | Horrobin |
| 2004/0018228 A1 | 1/2004 | Fischell et al. |
| 2004/0039441 A1 | 2/2004 | Rowland et al. |
| 2004/0058008 A1 | 3/2004 | Tarcha et al. |
| 2004/0060260 A1 | 4/2004 | Gottlieb et al. |
| 2004/0071756 A1 | 4/2004 | Fischell et al. |
| 2004/0072849 A1 | 4/2004 | Schreiber et al. |
| 2004/0092969 A1 | 5/2004 | Kumar |
| 2004/0102758 A1 | 5/2004 | Davila et al. |
| 2004/0117007 A1 | 6/2004 | Whitbourne et al. |
| 2004/0123877 A1 | 7/2004 | Brown et al. |
| 2004/0131755 A1 | 7/2004 | Zhong et al. |
| 2004/0133275 A1 | 7/2004 | Mansmann |
| 2004/0137066 A1 | 7/2004 | Jayaraman |
| 2004/0137179 A1 | 7/2004 | Matsuda et al. |
| 2004/0142094 A1 | 7/2004 | Narayanan |
| 2004/0146546 A1 | 7/2004 | Gravett et al. |
| 2004/0073284 A1 | 8/2004 | Bates et al. |
| 2004/0153125 A1 | 8/2004 | Roby |
| 2004/0156879 A1 | 8/2004 | Muratoglu et al. |
| 2004/0161464 A1 | 8/2004 | Domb |
| 2004/0167572 A1 | 8/2004 | Roth et al. |
| 2004/0170685 A1 | 9/2004 | Carpenter et al. |
| 2004/0192643 A1 | 9/2004 | Pressato et al. |
| 2004/0215219 A1 | 10/2004 | Eldridge et al. |
| 2004/0224003 A1 | 11/2004 | Schultz |
| 2004/0230176 A1 | 11/2004 | Shananhan et al. |
| 2004/0234574 A9 | 11/2004 | Sawhney et al. |
| 2004/0236278 A1 | 11/2004 | Herweek et al. |
| 2004/0241211 A9 | 12/2004 | Fischell et al. |
| 2004/0256264 A1 | 12/2004 | Israelsson et al. |
| 2005/0010078 A1 | 1/2005 | Jamiolkowski et al. |
| 2005/0025804 A1* | 2/2005 | Heller ................ A61K 31/41 424/423 |
| 2005/0042251 A1 | 2/2005 | Zhang et al. |
| 2005/0084514 A1 | 4/2005 | Shebuski et al. |
| 2005/0095267 A1 | 5/2005 | Campbell et al. |
| 2005/0100655 A1 | 5/2005 | Zhong et al. |
| 2005/0101522 A1 | 5/2005 | Speck et al. |
| 2005/0106206 A1 | 5/2005 | Herweek et al. |
| 2005/0106209 A1 | 5/2005 | Ameri et al. |
| 2005/0112170 A1 | 5/2005 | Hossainy et al. |
| 2005/0113687 A1 | 5/2005 | Herweek et al. |
| 2005/0113849 A1 | 5/2005 | Popadiuk et al. |
| 2005/0124062 A1 | 6/2005 | Subirade |
| 2005/0129787 A1 | 6/2005 | Murad |
| 2005/0154416 A1 | 7/2005 | Herweek et al. |
| 2005/0158361 A1 | 7/2005 | Dhondt et al. |
| 2005/0159809 A1 | 7/2005 | Hezi-Yamit et al. |
| 2005/0165476 A1 | 7/2005 | Furst et al. |
| 2005/0165477 A1 | 7/2005 | Anduiza et al. |
| 2005/0181061 A1 | 8/2005 | Ray et al. |
| 2005/0182485 A1 | 8/2005 | Falotico et al. |
| 2005/0186244 A1 | 8/2005 | Hunter et al. |
| 2005/0187376 A1 | 8/2005 | Pacetti |
| 2005/0203635 A1 | 9/2005 | Hunter et al. |
| 2005/0203636 A1 | 9/2005 | McFetridge |
| 2005/0223679 A1 | 10/2005 | Gottlieb et al. |
| 2005/0232971 A1 | 10/2005 | Hossainy et al. |
| 2005/0249775 A1 | 11/2005 | Falotico et al. |
| 2005/0283229 A1 | 12/2005 | Dugan et al. |
| 2006/0008501 A1 | 1/2006 | Dhont et al. |
| 2006/0020031 A1 | 1/2006 | Berlin |
| 2006/0036311 A1 | 2/2006 | Nakayama et al. |
| 2006/0051544 A1 | 3/2006 | Goldmann |
| 2006/0058737 A1 | 3/2006 | Herweek et al. |
| 2006/0058881 A1 | 3/2006 | Trieu |
| 2006/0064175 A1 | 3/2006 | Pelissier et al. |
| 2006/0067974 A1 | 3/2006 | Labrecque et al. |
| 2006/0067975 A1 | 3/2006 | Labrecque et al. |
| 2006/0067976 A1 | 3/2006 | Ferraro et al. |
| 2006/0067977 A1 | 3/2006 | Labrecque et al. |
| 2006/0067983 A1 | 3/2006 | Swanick et al. |
| 2006/0068674 A1 | 3/2006 | Dixit et al. |
| 2006/0078586 A1 | 4/2006 | Ferraro et al. |
| 2006/0083768 A1 | 4/2006 | Labrecque et al. |
| 2006/0088596 A1 | 4/2006 | Labrecque et al. |
| 2006/0093643 A1 | 5/2006 | Stenzel |
| 2006/0110457 A1 | 5/2006 | Labrecque et al. |
| 2006/0112536 A1 | 6/2006 | Herweek et al. |
| 2006/0121081 A1 | 6/2006 | Labrecque et al. |
| 2006/0124056 A1 | 6/2006 | Behnisch et al. |
| 2006/0134209 A1 | 6/2006 | Labhasetwar et al. |
| 2006/0158361 A1 | 7/2006 | Chou |
| 2006/0188607 A1 | 8/2006 | Schramm et al. |
| 2006/0204738 A1 | 9/2006 | Dubrow et al. |
| 2006/0210701 A1 | 9/2006 | Chappa et al. |
| 2006/0240069 A1 | 10/2006 | Utas et al. |
| 2006/0246105 A1 | 11/2006 | Molz et al. |
| 2006/0263330 A1 | 11/2006 | Emeta et al. |
| 2006/0269485 A1 | 11/2006 | Friedman et al. |
| 2007/0003603 A1 | 1/2007 | Karandikar et al. |
| 2007/0015893 A1 | 1/2007 | Hakuta et al. |
| 2007/0071798 A1 | 3/2007 | Herweek et al. |
| 2007/0084144 A1 | 4/2007 | Labrecque et al. |
| 2007/0093894 A1 | 4/2007 | Darouiche |
| 2007/0141112 A1 | 6/2007 | Falotico et al. |
| 2007/0198040 A1 | 8/2007 | Buevich et al. |
| 2007/0202149 A1 | 8/2007 | Faucher et al. |
| 2007/0212411 A1 | 9/2007 | Fawzy et al. |
| 2007/0218182 A1 | 9/2007 | Schneider et al. |
| 2007/0238697 A1 | 10/2007 | Jackson et al. |
| 2007/0264460 A1 | 11/2007 | Del Tredici |
| 2007/0275074 A1 | 11/2007 | Holm et al. |
| 2007/0276487 A1 | 11/2007 | Carleton et al. |

(56) References Cited

U.S. PATENT DOCUMENTS

| | | |
|---|---|---|
| 2007/0280986 A1 | 12/2007 | Gil et al. |
| 2007/0286891 A1 | 12/2007 | Kettlewell et al. |
| 2007/0299538 A1 | 12/2007 | Roeber |
| 2008/0016037 A1 | 1/2008 | Enomoto et al. |
| 2008/0038307 A1 | 2/2008 | Hoffmann |
| 2008/0044481 A1 | 2/2008 | Harel |
| 2008/0045557 A1 | 2/2008 | Grainger et al. |
| 2008/0071385 A1 | 3/2008 | Binette et al. |
| 2008/0086216 A1 | 4/2008 | Wilson et al. |
| 2008/0109017 A1 | 5/2008 | Herweck et al. |
| 2008/0113001 A1 | 5/2008 | Herweck et al. |
| 2008/0118550 A1 | 5/2008 | Martakos et al. |
| 2008/0160307 A1 | 7/2008 | Bauchet |
| 2008/0206305 A1 | 8/2008 | Herweck et al. |
| 2008/0207756 A1 | 8/2008 | Herweek et al. |
| 2008/0279929 A1 | 11/2008 | Devane et al. |
| 2008/0286440 A1 | 11/2008 | Scheer |
| 2008/0289300 A1 | 11/2008 | Gottlieb et al. |
| 2009/0011116 A1 | 1/2009 | Herweck et al. |
| 2009/0036996 A1* | 2/2009 | Roeber ............... A61F 2/0063 623/23.72 |
| 2009/0047414 A1 | 2/2009 | Corbeil et al. |
| 2009/0082864 A1 | 3/2009 | Chen et al. |
| 2009/0092665 A1 | 4/2009 | Mitra et al. |
| 2009/0099651 A1 | 4/2009 | Hakimi-Mehr et al. |
| 2009/0181074 A1 | 7/2009 | Makower ............... A61L 15/42 424/447 |
| 2009/0181937 A1 | 7/2009 | Faucher et al. |
| 2009/0186081 A1 | 7/2009 | Holm et al. |
| 2009/0208552 A1 | 8/2009 | Faucher et al. |
| 2009/0226601 A1 | 9/2009 | Zhong et al. |
| 2009/0240288 A1 | 9/2009 | Guetty |
| 2009/0259235 A1 | 10/2009 | Doucet et al. |
| 2009/0270999 A1 | 10/2009 | Brown |
| 2010/0183697 A1 | 7/2010 | Swanick et al. |
| 2010/0209473 A1 | 8/2010 | Dhont et al. |
| 2010/0233232 A1 | 9/2010 | Swanick et al. |
| 2010/0318108 A1 | 12/2010 | Datta et al. |
| 2011/0028412 A1 | 2/2011 | Cappello et al. |
| 2011/0045050 A1 | 2/2011 | Elbayoumi et al. |
| 2011/0144667 A1 | 6/2011 | Horton et al. |
| 2011/0213302 A1 | 9/2011 | Herweek et al. |
| 2011/0274823 A1 | 11/2011 | Labrecque et al. |
| 2012/0016038 A1 | 1/2012 | Faucher et al. |
| 2012/0213839 A1 | 8/2012 | Faucher et al. |
| 2012/0259348 A1 | 10/2012 | Paul |
| 2012/0315219 A1 | 12/2012 | Labrecque et al. |
| 2013/0041004 A1 | 2/2013 | Drager et al. |
| 2013/0084243 A1 | 4/2013 | Goetsch et al. |
| 2013/0096073 A1 | 4/2013 | Sidelman |

FOREIGN PATENT DOCUMENTS

| | | |
|---|---|---|
| CN | 101448474 A | 6/2009 |
| CN | 102256565 A | 11/2011 |
| DE | 19916086 A1 | 10/1999 |
| DE | 10115740 A1 | 10/2002 |
| EP | 0471566 A1 | 2/1992 |
| EP | 0610731 A1 | 8/1994 |
| EP | 0623354 A1 | 9/1994 |
| EP | 0655222 B1 | 11/1994 |
| EP | 0730864 A1 | 11/1996 |
| EP | 0790822 B1 | 8/1997 |
| EP | 0873133 B1 | 10/1998 |
| EP | 0950386 A2 | 4/1999 |
| EP | 0917561 B1 | 5/1999 |
| EP | 1132058 A1 | 9/2001 |
| EP | 1140243 B1 | 10/2001 |
| EP | 1181943 A1 | 2/2002 |
| EP | 1402906 A1 | 6/2002 |
| EP | 1219265 A2 | 7/2002 |
| EP | 1270024 A1 | 1/2003 |
| EP | 1273314 A1 | 1/2003 |
| EP | 1364628 A1 | 11/2003 |
| EP | 1520795 A1 | 4/2005 |
| EP | 1557183 A1 | 7/2005 |
| EP | 1576970 A1 | 9/2005 |
| EP | 1718347 A | 9/2005 |
| EP | 2201965 A1 | 6/2010 |
| EP | 2083875 B1 | 3/2013 |
| GB | 2363572 A | 1/2002 |
| JP | 49050124 A | 5/1974 |
| JP | S61291520 A | 12/1986 |
| JP | H01175864 A | 7/1989 |
| JP | H01503296 A | 11/1989 |
| JP | H08224297 A | 9/1996 |
| JP | 200110958 A | 1/2001 |
| JP | 2006512140 A | 4/2006 |
| JP | 2008155014 A | 7/2008 |
| JP | 2012505025 A | 3/2012 |
| JP | 2012505030 A | 3/2012 |
| JP | 2013508033 A | 3/2013 |
| KR | 20080025986 A | 3/2008 |
| RU | 2125887 C1 | 2/1999 |
| SU | 1297865 A1 | 3/1987 |
| WO | 198600912 A1 | 2/1986 |
| WO | 198706463 A1 | 11/1987 |
| WO | 199001969 A1 | 3/1990 |
| WO | 90/008544 A1 | 8/1990 |
| WO | 199321912 A1 | 11/1993 |
| WO | 199517901 A1 | 7/1995 |
| WO | 199526715 A2 | 10/1995 |
| WO | 199618417 A1 | 6/1996 |
| WO | 199641588 A1 | 12/1996 |
| WO | 199702042 A1 | 1/1997 |
| WO | 199709367 A1 | 3/1997 |
| WO | 199713528 A1 | 4/1997 |
| WO | 199823228 A1 | 6/1998 |
| WO | 199830206 A1 | 7/1998 |
| WO | 98/46287 A2 | 10/1998 |
| WO | 199854275 A2 | 12/1998 |
| WO | 199908544 A1 | 2/1999 |
| WO | 199925336 A1 | 5/1999 |
| WO | 199927989 A1 | 6/1999 |
| WO | 199940874 A1 | 8/1999 |
| WO | 199956664 A1 | 11/1999 |
| WO | 200012147 A1 | 3/2000 |
| WO | 200040236 A1 | 7/2000 |
| WO | 200040278 A1 | 7/2000 |
| WO | 200053212 A1 | 9/2000 |
| WO | 200062830 A2 | 10/2000 |
| WO | 200115764 A1 | 3/2001 |
| WO | 200124866 A1 | 4/2001 |
| WO | 200126585 A1 | 4/2001 |
| WO | 200137808 A1 | 5/2001 |
| WO | 200145763 A1 | 6/2001 |
| WO | 200160586 A1 | 8/2001 |
| WO | 200166036 A2 | 9/2001 |
| WO | 200176649 A1 | 10/2001 |
| WO | 200185060 A1 | 11/2001 |
| WO | 200222047 A1 | 3/2002 |
| WO | 200222199 A2 | 3/2002 |
| WO | 200249535 A2 | 6/2002 |
| WO | 2002076509 A2 | 10/2002 |
| WO | 2002100455 A2 | 12/2002 |
| WO | 2003000308 A1 | 1/2003 |
| WO | 2003015748 A2 | 2/2003 |
| WO | 2003028622 A2 | 4/2003 |
| WO | 2003037397 A2 | 5/2003 |
| WO | 2003037398 A2 | 5/2003 |
| WO | 2003039612 A1 | 5/2003 |
| WO | 2003041756 A1 | 5/2003 |
| WO | 2003070125 A1 | 8/2003 |
| WO | 2003073960 A1 | 9/2003 |
| WO | 2003092741 A1 | 11/2003 |
| WO | 2003092779 A1 | 11/2003 |
| WO | 2003094787 A1 | 11/2003 |
| WO | 2003105727 A1 | 12/2003 |
| WO | 2004004598 A2 | 1/2004 |
| WO | 2004006976 A1 | 1/2004 |
| WO | 2004006978 A1 | 1/2004 |
| WO | 2004028582 A2 | 4/2004 |
| WO | 2004028583 A2 | 4/2004 |

(56) References Cited

FOREIGN PATENT DOCUMENTS

| WO | 2004028610 | A2 | 4/2004 |
|---|---|---|---|
| WO | 2004091684 | A1 | 10/2004 |
| WO | 2004101010 | A1 | 11/2004 |
| WO | 2005000165 | A1 | 1/2005 |
| WO | 2005016400 | A1 | 2/2005 |
| WO | 2005053767 | A1 | 6/2005 |
| WO | 2005073091 | A2 | 8/2005 |
| WO | 2005082434 | A2 | 9/2005 |
| WO | 2005116118 | A1 | 12/2005 |
| WO | 2006024488 | A2 | 3/2006 |
| WO | 2006032812 | A3 | 3/2006 |
| WO | 2006036967 | A1 | 4/2006 |
| WO | 2006102374 | A2 | 9/2006 |
| WO | 2007047781 | A2 | 4/2007 |
| WO | 2007047028 | A1 | 5/2007 |
| WO | 2008/010788 | A2 | 1/2008 |
| WO | 2008/016664 | A2 | 2/2008 |
| WO | 2008039308 | A2 | 4/2008 |
| WO | 2008057328 | A2 | 5/2008 |
| WO | 2009091900 | A1 | 7/2009 |
| WO | 2010/042134 | A1 | 4/2010 |
| WO | 2010/042241 | A1 | 4/2010 |
| WO | 2012009707 | A2 | 1/2012 |

OTHER PUBLICATIONS

H. Fineberg et al., Industrial Use of Fish Oils, pp. 222-238, http://spo.nmfs.noaa.gov/Circulars/CIRC278.pdf, downloaded Aug. 3, 2015.
Lewis, Richard J., Sr., Hawley's Condensed Chemical Dictionary, 2001, pp. 308, 309 and 896-898, 14th edision, John Wiley & Sons, Inc., New York.
Webster's II New College Dictionary (1995), 1075, Houghton Mifflin Company, New York, US.
Polymers made from multiple monomers, A Natural Approach to Chemistry, Chapter 8, 241, http://lab-aids.com/assets/uploads/NAC/NAC_student_book/Texas%20Student%20Edition%20253.pdf (downloaded Dec. 3, 2015).
Polymer, Encyclopedia Britannica. Encyclopedia Britannica Online, Encyclopedia Britannica Inc., 105, Web. Dec. 2, 2015, http://www.britannica.com/print/article/468696 (downloaded Dec. 2, 2015).
SepraFilm Adhesion Barrier package insert (Genzyme Biosurgery 2008).
Sannino, Alessandro, et al., Biodegradeable Cellulose-based Hydrogels: Design and Applications, 2 Materials, pp. 353-373, 2009.
Heinz, Thomas, Carboxymethyl Ethers of Cellulose and Starch—A Review, Center of Excellence for Polysaccharide Research, Friedrich Schiller University of Jena (Germany), pp. 13-29, 2005.
Omidian, H. et al., Swelling Agents and Devices in Oral Drug Delivery, J. Drug. Del. Sci. Tech., No. 18, vol. 2, 2008, pp. 83-93.
Kamel, S. et al., Pharmaceutical Significance of Cellulose: A Review, Express Polymer Letters vol. 2, No. 11, 2008, pp. 758-778.
Adel, A. M. et al., Carboxymethylated Cellulose Hydrogel: Sorption Behavior and Characterization, Nature and Science, No. 8, vol. 8, 2010, pp. 244-256.
Bacteria in Water, The USGS Water Science School, http://water.usgs.goviedu/bacteria.html (downloaded Nov. 9, 2015).
Novotny, L. et al., Fish: a potential source of bacterial pathogens for human beings, Vet. Med.—Czech, 49, 2004, vol. 9, pp. 343-358.
Allergies, Asthma and Allergy Foundation of America (2011), http://www.aafa.org/page/types-of-allergies,aspx (downloaded Oct. 5, 2015).
Sicherer, Scott H., Food Allergies: A Complete Guide for Eating When Your Life Depends on it, 2013, 15, Johns Hopkins University Press, Baltimore, MD, USA.
Dmega-3 DHA—The Problem May Be the Quality of Your Fish Oil, Not Your Allergy to Fish, Fatty Acids Hub, http://www.fattyacidshub.com/fatty-acids/omega-3-dha/ (downloaded Nov. 10, 2015).

Soy Allergy, Asthma and Allergy Foundation of America (2005), http://www.aafa.org/display.cfm? id=9&sub=20&cont=522 (downloaded Nov. 10, 2015).
Refined soybean oil not an allergen, say food scientists, FOOD navigator-usa.com (2005), http://www.foodnavigator-usa.com/content/view/print/127438 (downloaded Nov. 10, 2015).
Yahyaee, R. et al., Waste fish oil biodiesel as a source of renewable fuel in Iran, Renewable and Sustainable Energy Reviews, 2013, pp. 312-319, 17, Elsevier Ltd.
Biological evaluation of medical devices—Part 1: Evaluation and testing, International Standard ISO 109931-1, Aug. 1, 2003, Third Edition, Switzerland.
Mayo Clinic (http://www.mayoclinic.org/drugs-supplements/omega-3-fatty-acids-fish-oil-alpha-linolenic-acids/safety/nrb-20059372?p=1 (downloaded Sep. 28, 2015).
Milk allergy, at http://www.mayoclinic.org/diseases-conditions/milk-allergy/basics/definition/con-20032147?p=1 (downloaded Jul. 29, 2015).
Soy allergy, at http://www.mayoclinicorg/diseases-conditions/soy-allergy/basics/definition/con-20031370?p=1 (downloaded Jul. 29, 2015).
F.D. Gunstone, Fatty Acid and Lipid Chemistry 72 (1999).
Hawley's Condensed Chemical Dictionary 315, 316, 332, 333, 334, 825 and 826 (2001).
Hutlin, Herbert O. et al., Chemical Composition and Stability of Fish Oil (International Association of Fish Meal Manufacturers Apr. 10, 1991).
F.V.K Young, The Chemical & Physical Properties of Crude Fish Oils for Refiners and Hydrogenators, 18 Fish Oil Bulletin 1-18 (1986).
Karrick, Neva L., Nutritional Value of Fish Oils as Animal Feed, Circular 281 (Fish and Wildlife Service Bureau of Commercial Fisheries 1967), reprinted from M.E. Stansby (ed.), Fish Oils 362-382 (Avi Publishing Company 1967).
Luley et al., Fatty acid composition and degree of peroxidation in fish oil and cod liver oil preparations, Arzneimittelforschung. Dec. 1998, vol. 38, No. 12, pp. 1783-1786.
Drying Oil, http://en.wikipedia.org/wiki/drying_oil (downloaded Jun. 28, 2013).
Szebeni et al., "Complement Activation by Cremophor EL as a Possible Contributor to Hypersensitivity to Paclitaxel: an in Vitro Study", Journal of the National Cancer Institute, 1998, vol. 90, No. 4, pp. 300-306.
Birsan, et al., "The novel calcineurin inhibitor ISA247: a more potent immunosuppressant than cyclosporine in vitro", Transpl. Int., 2005, vol. 17, pp. 767-771.
About.com, "Orthopedics, Synvisc injections," retrieved online at http://orthopedics.about.com/cs/treatment/a/synvisc_2.htm (2005).
Cath Lab Digest, "Olive Oil Emulsion Helps With Problem Heart Arteries", retrieved online at http://www.cathlabdigest.com/displaynews.cfm?newsid=0103073 (2007).
Doctor's Guide to Medical and Other News, "AAOS Meeting: Synvisc Delays Total Knee Replacement in Osteoarthritis Patients", retrieved online at http://www.docguide.com/dg.nsf/PrintPrint/4585EC355198EEF08525670E006B10FF (1999).
Methodist, "Evaluation of Biocompatibility and Antirestenotic Potential of Drug Eluting Stents Employing Polymer-free Highly-Hydrogenated Lipid-Based Stent Coatings in Porcine Coronary Arteries", Transcatheter Cardiovascular Therapeutics (TCT), sponsored by the Cardiovascular Research Foundation®, Oct. 22-27, 2006, Washington Convention Center, Washington, D.C.
Novavax, retrieved online at http://www.novavax.com/go.cfm?do=Page.View&pid=3 (2006).
Orthovisc, "New Treatment Option is Potential Alternative to OTC Pain Medications for Osteoarthritis of the Knee" retrieved online at http://www.jnj.com/innovations/new_features/ORTHOVISC.htm:lessionid=33N2RBQDV0DZKCQPCCEGU3AKB2IIWTT1 (2006).
Orthovisc, "What is ORTHOVISC®?" retrieved online at http://www.orthovisc.com/xhtmlbgdisplay.jhtml? temname=about_orthovisc (2005).

(56) References Cited

OTHER PUBLICATIONS

Orthovisc, "Your Knees and Osteoarthritis", retrieved online at http://www.orthovisc.com/xhtmlbgdisplay.jhtml? temname=understanding_knee_oa (2003).

Orthovisc, "What to expect from your treatment," retrieved online at http://www.orthovisc.com/xhtmlbgdisplay.jhtml? temname=what_to_expect (2007).

Orthovisc, "Tools and Resources for Managing Your Osteoarthritis", retrieved online at http://www.orthovisc.com/xhtmlbgdisplay.jhtml? itemname=patient_resources (2007).

Pohibinska, A., et al., "Time to reconsider saline as the ideal rinsing solution during abdominal surgery", The American Journal of Surgery, vol. 192, pp. 281-222 (2007).

Singh, Alok, et al., "Facilitated Stent Delivery Using Applied Topical Lubrication", Catherization and Cardiovascular Interventions, vol. 69, pp. 218-222 (2007).

Urakaze, Masaharu et al., "Infusion of fish oil emulsion: effects on platelet aggregation and fatty acid composition in phospholipids of plasma, platelets and red blood cell membranes in rabbits", Am. J. Clin. Nutr., vol. 46, pp. 936-940 (!387).

Hortolam, Juliane G., et al., "Connective tissue diseases following silicone breast implantation: where do we stand?", Clinics, 2013, vol. 3, p. 281.

Lidar, M. et al., "Silicone and sclerodema revisited", Lupus, 2012, vol. 21, pp. 121-127.

Swanson, Danielle, et al., Omega-3 Fatty Acids EPA and DHA: Health Benefits Throughout Life, 3 Advances in Nutrition 1-7 (American Society for Nutrition 2012).

Triglycerides, https://www.lipid.org/sites/default/files/triglycerides.pdf (downloaded Sep. 24, 2015).

Fish Oil Triglycerides vs. Ethyl Esters: A Comparative Review of Absorption, Stability and Safety Concerns (Ascenta Health Ltd. 2010 at http://www.ascentaprofessional.com/science/articles/fish-oil-triglycerides-vs-ethyl-esters (downloaded Sep. 24, 2015).

Fats & Oils (2008) at http://scifun.chem.wisc.edu/chemweek/pdf/fats&oils.pdf (downloaded Sep. 24, 2015).

"Lead", Article by Centers for Disease Control and Prevention (CDC), Nov. 2009, 2 pages.

Erhan et al., Vegetable-oil-based printing ink formulation and degradation, Industrial Crops and Products, 1995, 237-246, 3.

Non-Final Office Action issued in U.S. Appl. No. 15/710,514, dated Sep. 17, 2018.

Non-Final Office Action dated Oct. 5, 2018 for related case U.S. Appl. No. 15/819,304, filed Nov. 21, 2017, 8 pages.

Office Action issued in European Application No. 10825447.5 dated Jul. 25, 2019, 6 pages.

Oliveira, Fernanda L.C., et al., Triglyceride Hydrolysis of Soy Oil vs Fish Oil Emulsions, Journal of Parenteral and Enteral Nutrition, Jul./Aug. 1997, 224-229, vol. 21, No. 4.

Wagner, Karl-Heinz, et al., Effects of tocopherols and their mixtures on the oxidative stability of olive oil and linseed oil under heating, Eur. J. Lipid Sci. Technol., 2000, 624-629, 102.

Non-Final Office Action issued in U.S. Appl. No. 16/165,628, dated Oct. 28, 2019.

Notice of Allowance issued in U.S. Appl. No. 15/841,993, dated Oct. 30, 2019.

Hogg, Ronald J., et al., Clinical Trial to Evaluate Omega-3 Fatty Acids and Alternate Day Prednisone in Patients with IgA Nephropathy: Report from the Southwest Pediatric Nephrology Study Group, Clin J Am Soc Nephrol 1, Apr. 12, 2006, 467-474.

Bruno, Gene, Omega-3 Fatty Acids, Literature Education Series on Dietary Supplements, 2009, 1-4, Huntington College of Health Sciences, Knoxville, TN, US.

Mateo, R. D., et al., Effect of dietary supplementation of n-3 fatty acids and elevated concentrations of dietary protein on the performance of sows, J. Anim. Sci., 2009, 948-959, 87.

Genzyme Corporation, 510(k) Notification, Section 10: 510(k) Summary, Dec. 21, 1999, 11 pages.

Deeken, Corey R., et al., A review of the composition, characteristics, and effectiveness of barrier mesh prostheses utilized for laparoscopic ventral hernia repair, Surg Endosc, 2011, 10 pages.

Timar-Balzsy et al., Chemical Principles of Textile Conservation, Oxford: Elsevier Science Ltd., 1998, pp. 117-119.

CECW-EE, "Ch. 4: Coating Types and Characteristics", Engineering and Design—Painting: New Construction and Maintenance, 1995, pp. 4-1 to 4-24.

Wikipedia, "Sirolimus", pp. 1-13, available online at http://en.wikipedia.org/wiki/sirolimus, accessed May 11, 2011.

Binder et al., "Chromatographic Analysis of Seed Oils_ Fatty Acid Composition of Castor Oil", The Journal of American Oil Chemists' Society, 1962, vol. 39, pp. 513-517.

Supplementary ESR in EP05804291, dated Jul. 26, 2011.

Supplementary ESR in EP05802894 dated Jul. 27, 2011.

Supplementary ESR in EP05800844 dated Aug. 19, 2011.

Crivello et al., "Epoxidized triglycerides as renewable monomers in photoinitiated cationic polymerization", Chem. Mater. 1992, pp. 692-699.

Supplementary ESR in EP05858430 dated Aug. 18, 2011.

Encyclopedia Britannica Online, "Surface Coating", available online at http://www.britannica.com/Ebchecked/topic/575029/surface-coating>, accessed Jun. 17, 2011.

Supplementary European Search Report for Application No. EP 08877338.7 dated Aug. 16, 2012.

Supplementary European Search Report for Application No. EP09819594.4, dated Aug. 14, 2012.

International Search Report for PCT/US2011/44292, dated Dec. 6, 2011.

Ahuja et al., "Prevention of Postoperative Intraperitoneal Adhesions—An Experimental Study in Rats", Journal of Indian Pediatric Surgery 2002 7:15-20.

Jonasson, Lena et al., "Cyclosporon A inhibits smooth muscle proliferation in the vascular response to injury," Proc. Natl. Acad. Sci. USA, vol. 85: 2303-2306 (1988).

Ogunniyi, D.S., "Castor oil: A vital industrial raw material," Biosource Technology, vol. 97: 1086-1091 (2006).

Redman, L.V. et al., "The drying rate of raw paint oils—a comparison," The Journal of Industrial and Engineering Chemistry, vol. 5: 630-636 (1913).

Rutkow, Ira M. et al., "'Tension-free' inguinal herniorrhaphy: A preliminary report on the 'mesh plug' technique," Surgery, vol. 114:3-8 (1993).

Websters Dictionary Online, Accessed on Feb. 13, 2009, entry for "polymer".

International Search Report for International Application PCT/US05/034941, dated May 4, 2006.

Ackman, R.G., "Fish Oils", Bailey's Industrial Oil and Fat Products, 6th Edition, 279-317 (2005).

Andres, et al. "Antiproliferative Strategies for the Treatment of Vascular Proliferative Disease", Current Vascular Pharmacology, 1)1): 85-98 (2003).

Winter, et al., "Physical and Chemical Gelation" Encyclopedia of Materials—Science and Technology, vols. 1-11: 6691-6999 (2001).

Supplementary European Search Report for EP12004057 dated Apr. 10, 2013.

Lipids, Chapter 19, pp. 1-12 (2002).

Jorge, et al. Influence of fatty acid composition on the formation of polar glycerides and polar fatty acids in sunflower pils heated at frying temperatures, Grasas y Aceites, 48(1): 17-24, (1997).

International Search Report for International Application PCT/US2013/044653, dated Sep. 4, 2013.

Mallegol, "Long-Term Behavior of Oil-Based Varnishes and Paints Photo-and Thermooxidation of Cured Linseed Oil", Journal of the American Oil Chemists' Society, 77:257-263 (2000).

Supplementary European Search Report for Application No. EP 10825447, dated Mar. 31, 2014.

Uchida, et al., "Swelling Process and Order-Disorder Transition of Hydrogel Containing Hydrophobic Ionizable Groups", Macromolecules, 28, 4583-4586 (1995).

Gutfinger, et al., "Polyphenols in Olive Oils", Journal of the American Oil Chemists Society, 58(11): 966-968 (1981).

(56) References Cited

OTHER PUBLICATIONS

De la Portilla, et al., "Prevention of Peritoneal Adhesions by Intraperitoneal Administration of Vitamin E: An Experimental Study in Rats", Diseases of the Colon and Rectum, 47; 2157-2161 (2005).
Sano, et al., "A controlled Trial of Selegiline, Alpha-Tocopherol, or Both as Treatment for Alzheimer's Disease", The New England Journal of Medicine, 336; 1216-1222 (1997).
Wikipedia, Sunflower oil, accessed Jul. 23, 2015, pp. 1-7.
Esoteric Oils, Peppermint essential oil information, accessed Jul. 23, 2015, pp. 1-7.
Orthomolecular, Fish Oil, Jun. 29, 2004, http://orthomolecular.org/nutrients/fishoil.html, accessed Jul. 22, 2015, p. 1.
Wicks et al. Organic Coatings:Science and Technology 1999 New York:Wiley Interscience p. 258-267.
Mills et al. Oils and Fats. "The Organic Chemistry of Museum Objects" London:Buttersworth and Co. 1987, p. 26-40.
Erhardt, "Paints Based on Drying Oil Media". Painted Wood: History & Conservation. Ed. Berland Singapore: The J. Paul Getty Trust, 1998. p. 17-32.
Wexler et al. Chemical Reviews 1964 64(6):591-611.
Polymer—The Chambers 21st Century Dictionary M. Robinson and G. Davidson (Eds.), London, United Kingdom: Chambers Harrap. Retrieved from http://search.credoreference.com/content/entry/chambdict!polymer/O; 2001.
Polymer—Academic Press Dictionary of Science and TechnologyC. Morris (Ed.), Academic Press Dictionary of Science and Technology. Oxford, United Kingdom: Elsevier Science & Technology. Retrieved from http://search.credoreference.com/content/entry/apdst!polymer/O; 1992.
Falagas et al. European Society of Clinical Microbiology and Infection Diseases 2005 11:3-8.
Bimbo "International Fishmeal & Oil Manufactures Association, Guidelines for Characterising Food Grade Fish Oil", (INFORM 1998 9(5):473-483.
Mallegol et al. Drier influence on the curing of linseed oil, Progress in Organic Coatings, Nov. 2000, vol. 39, No. 2, pp. 107-113.
Morse, Molecular distillation of polymerized drying oils, Ind. Eng. Chem., 1941, No. 33, pp. 1039-1043.
Shengqiao, "Evaluation of the Biocompatibility and Drug Delivery Capabilities of Biological Oil Based Stent Coatings", Katholieke Universiteit Leuven, 63 pages.
Autosuture, "Parietex TM Composite OS SERIES MESH", retrieved online at http://www.autosuture.com/AutoSuture/pagebuilder.aspx?topicID=135734&breadcrumbs=135601:0 (2007).
Camurus, "In our endeavors to create the unique, we start with the best. Your product".
De Scheerder, Ivan K. et al., "Biocompatibility of polymer-coated oversized metallic stents implanted in normal porcine coronary arteries", Atherosclerosis, vol. 114, pp. 105-114; 1995.
Office Action issued in Chinese Application No. 201610998395.8 dated Apr. 28, 2020, 14 pages.
Office Action issued in Chinese Application No. 201610997993.3 dated May 11, 2020, 7 pages.
Final Office Action issued in U.S. Appl. No. 16/165,628 dated Apr. 13, 2020, 9 pages.
Final Office Action for U.S. Appl. No. 11/238,554, dated May 1, 2009.
Non-final Office Action for U.S. Appl. No. 11/238,554, dated Jul. 25, 2008.
Non-final Office Action for U.S. Appl. No. 11/238,564 dated Apr. 16, 2008.
Final Office Action for U.S. Appl. No. 11/238,564 dated Aug. 6, 2009.
Non-final Office Action for U.S. Appl. No. 11/239,555 dated Mar. 30, 2009.
Non-final Office Action for U.S. Appl. No. 11/525,328 dated Apr. 30, 2007.
Non-final Office Action for U.S. Appl. No. 11/525,390 dated Jul. 14, 2010.
Final Office Action for U.S. Appl. No. 11/525,390 dated Apr. 21, 2011.
Final Office Action for U.S. Appl. No. 11/582,135 (listed on SB/08 as US 2007/0202149, dated May 12, 2011.
Non-final Office Action for U.S. Appl. No. 11/582,135 dated Nov. 9, 2010.
Non-final Office Action for U.S. Appl. No. 11/582,135, dated Jan. 6, 2010.
Non-final Office Action for U.S. Appl. No. 11/582,135 dated May 12, 2009.
Non-final Office Action for U.S. Appl. No. 11/701,799 dated Apr. 12, 2010.
Non-final Office Action for U.S. Appl. No. 11/978,840 dated Dec. 3, 2010.
Non-final Office Action for U.S. Appl. No. 11/980,155 dated Mar. 24, 2011.
Non-final Office Action for U.S. Appl. No. 12/075,223 dated Dec. 8, 2010.
Non-final Office Action for U.S. Appl. No. 12/325,546 dated Feb. 25, 2010.
Final Office Action for U.S. Appl. No. 12/325,546 dated Aug. 31, 2010.
Non-final Office Action for U.S. Appl. No. 12/364,763 dated Dec. 11, 2009.
Final Office Action for U.S. Appl. No. 12/364,763, dated Sep. 21, 2010.
Interview summary for U.S. Appl. No. 11/236,908 dated May 5, 2009.
Interview summary for U.S. Appl. No. 11/236,908 dated Dec. 2, 2010.
Interview summary for U.S. Appl. No. 11/582,135 dated Dec. 7, 2010.
Interview summary for U.S. Appl. No. 12/325,546 dated Dec. 2, 2010.
Interview summary for U.S. Appl. No. 12/364,763 dated Dec. 2, 2010.
Final Office Action for U.S. Appl. No. 11/978,840, dated Jun. 22, 2011.
Non-final Office Action for U.S. Appl. No. 11/525,390 dated Jul. 11, 2011.
Non-Final Office Action for U.S. Appl. No. 11/701,799 dated Aug. 17, 2011.
Final Office Action for U.S. Appl. No. 11/980,155 dated Oct. 21, 2011.
Non-Final Office Action for U.S. Appl. No. 12/182,261 dated Dec. 21, 2011.
Non-Final Office Action for U.S. Appl. No. 11/236,908 dated Dec. 2, 2011.
Non-Final Office Action for U.S. Appl. No. 11/582,135 dated Oct. 14, 2011.
Non-Final Office Action for U.S. Appl. No. 12/182,165 dated Jan. 5, 2012.
Non-Final Office Action for U.S. Appl. No. 12/401,243, dated Jan. 5, 2012.
Notice of Allowance for U.S. Appl. No. 11/582,135 dated Jan. 9, 2012.
Final Office Action for U.S. Appl. No. 12/075,223 dated Aug. 11, 2011.
Multanen, M., et al., Bacterial adherence to silver nitrate coated poly-L-lactic acid urological stents in vitro, Urol Res., Oct. 2000, 327-31, 5. (Abstract).
Douglas, Kyle, et al., Zero-Order Controlled-Release Kinetics Through Polymer Matrices, available at http://www.drew.edu/wp-content/uploads/sites/99/Team5.pdf (downloaded Dec. 21, 2016).
Kaczynski, Jason, "Natural Omega3 Fish Oil Supplements—How to Avoid Synthetic Fish Oils," accessed online at http://ezinearticles.com/?Natural-Omega3-Fish-Oil-Supplements—How-to-Avoid-Synthetic-Fish-Oils&id=2460278, Jun. 10, 2009.
Luostarinen et al., "Vitamin E supplementation counteracts the fish oil induced increase of blood glucose in humans," Nutrition Research, vol. 15, No. 7, pp. 953-968, 1995.
The Lipid Handbook, 2nd edision, 1994, Tocopherols, pp. 129-131.
Non-Final OA for U.S. Appl. No. 121767,289 mailed Mar. 15, 2012.

(56) References Cited

OTHER PUBLICATIONS

ISR for PCT/BE02/00166, dated Apr. 3, 2003.
ESR for EP Application 05012112, dated Jul. 5, 2005.
ESR for EP Application 10157210, dated May 20, 2010.
Non-Final OA for U.S. Appl. No. 11/140,811 mailed Sep. 15, 2008.
Final OA for U.S. Appl. No. 11/140,811 mailed Nov. 25, 2009.
Non-Final OA for U.S. Appl. No. 121767,289 mailed Aug. 19, 2011.
De Scheerder et al., "Local Angiopeptin Delivery Using Coated Stents Reduces Neointimal Proliferation in overstretched Porcine Coronary Arteries," J. Invasive Cardiol., 1995, vol. 8, pp. 215-222.
De Scheerder et al., "Experimental Study of Thrombogenicity and Foreign Body Reaction Induced by Heparin-Coated Coronary Stents," Circulation, 1997, vol. 95, pp. 1549-1553.
Nakatsuji et al. "Antimicrobial Property of Lauric Acid Against Propionibacterium acnes: Its Thereapeutic Potential for Inflammatory Acne Vulgarisu" Journal of Investigative Dermatology 2009 129(10): 2480-2488.
Gervajio "Fatty Acids and Derivatives from Coconut Oil." Baileys Industrial Oil and Fat Products, Sixth Edition. Ed. Sahandi. Hoboken: John Wiley & Sons, Inc. 2005 1-3.
Pandey et al. "Solid lipid particle-based inhalable sustained drug delivery system against experiemental tuberculosis" Tuberculosis 2005 85:227-234.
Web article from http://www.buchi.com, "Slip Melting Point Determination of Palm Stearin", 1 page.
Notice of Allowance for U.S. Appl. No. 11/525,390, dated Nov. 30, 2012.
Interview summary for U.S. Appl. No. 11/237,420 dated May 5, 2009.
American heritage desk dictionary, 1981. p. 799, 2 pages.
John McMurray, Organic Chemistry, third edition, 1992, pp. 45-48.
9.1 Terminology for Vegetable Oils and Animal Fats, at http://www.e-education.psu.edu/egee439/node/683 (downloaded Sep. 13, 2017), pp. 1-8.
Sunflower Oil, at https//en.wikipedia.org/wiki/Sunflower_oil (downloaded Sep. 19, 2017, pp. 1-8.
Fatty Acid Composition of Marine Oils by GLC, AOCS Official Method Ce 1b-89 (2009), pp. 1-7.
Preparation of Methyl Esters of Fatty Acids, AOCS Official Method Ce 2-66 (2009), pp. 1-2.
European Extended Search Report dated Jan. 18, 2016, issued for corresponding EP Patent Application No. 11807612.4, 7 pages.
International Preliminary Report on Patentability for Application No. PCT/US08/85386, dated Apr. 12, 2011.
International Search Report for Application No. PCT/US10/048167, dated Oct. 20, 2010.
Non-Final Office Action for U.S. Appl. No. 12/401,228, dated Nov. 12, 2010.
Non-Final Office Action for U.S. Appl. No. 11/711,389, dated Dec. 17, 2010.
Final Office Action for U.S. Appl. No. 11/250,768, dated Nov. 9, 2010.
Drummond, Calum J. et al., "Surfactant self-assembly objects as novel drug delivery vehicles", Current Opinion in Colloid & Interface Science, 2000, vol. 4, pp. 449-456.
Engstrom, Sven, "Drug Delivery from Cubic and Other Lipid-water Phases", Lipid Technology, 1990, vol. 2, No. 2, pp. 42-45.
Guler et al., "Some empirical equations for oxopolymerization of linseed oil", Progress in Organic Coatings, 2004, vol. 51, pp. 365-371.
Hwang, Chao-Wei et al., "Physiological Transport Forces Govern Drug Distribution for Stent-Based Delivery", Circulation, 2001, vol. 104, pp. 600-605.
Oberhoff, Martin et al., "Local and Systemic Delivery of Low Molecular Weight Heparin Following PTCA: Acute Results and 6-Month Follow-Up of the Initial Clinical Experience With the Porous Balloon (PILOT—Study)," Catheterization and Cardiovascular Diagnosis, 1998, vol. 44, pp. 267-274.
Polymerization, Merriam-Webster Online Dictionary, retrieved from www.merriam-webster.com on Dec. 13, 2009.
Salu, Koen J. et al., "Addition of cytochalasin D to a biocompatible oil stent coating inhibits intimal hyperplasia in a porcine coronary model", Coronary Artery Disease, 2003, vol. 14, No. 8, pp. 545-555.
Scheller, Bruno et al., "Addition of Paclitaxel to Contrast Media Prevents Restenosis After Coronary Stent Implantation", Journal of the American College of Cardiology, 2003, vol. 42, No. 8, pp. 1415-1420.
Shahidi, Fereidoon ed.; "Bailey's Industrial Oil and Fats Products" 2005: John Wiley and Sons; vol. 5, Edible Oil and Fat Products, Processing Technologies, pp. 1-15.
Van Der Giessen, Willem J. et al., "Marked inflammatory Sequelae to Implantation of Biodegradable and Nonbiodegradable Polymers in Porcine Coronary Arteries", Circulation, 1996, vol. 94, pp. 1690-1697.
Cure; in Academic Press Dictionary of Science and Technology, 1992.
Erhan, Sevim, et al., "Vegetable-oil-based printing ink formulation and degradation", Industrial Crops and Products 3, 1995, pp. 237-246.
Evans, D.F., et al., Measurement of gastrointestinal pH profiles in normal ambulant human subjects, GUT, 1988, 1035-1041, 29.
Final Office Action issued in U.S. Appl. No. 12/581,582, dated Jan. 8, 2015.
Non-Final Office Action for U.S. Appl. No. 12/581,582, dated May 29, 2014.
Office Action issued in EP Application No. 10825447.5, dated Jul. 25, 2019.
Petrovic, Z. S., Polymers from biological oils, Contemporary Materials, 1-1, 2010, 39-50.
Sahni, "A Review on Spider Silk Adhesion", The Journal of Adhesion, 2011, 595-614, 87.
"What are Omega-9 Fats?", Paleo Leap, LLC, printed from http://paleoleap.com/omega-9-fats on Sep. 14, 2016, 5 pages.
Kumar, Ashavani, et al., "Silver-nanoparticle-embedded antimicrobial paints based on vegetable oil", Nature Materials, vol. 7, Mar. 2008, pp. 236-241.
Shriner et al., "The Systematic Identification of Organic Compounds—a laboratory manual", pp. 284 and 285, 6th ed. (John Wiley & Sons—1980).
Olive Oil Reference Book (PerkinElmer, Inc. 2012), pp. 1-4.
Standard for Olive Oils and Olive Pomace Oils, Codex Stan 33-1981 (World Health Organization 2013), pp. 1-9.
Wei Wang et al., "Directing Oleate Stabilized Nanosized Silver Colloids into Organic Phases", Langmuir, vol. 14, No. 3, (1998), pp. 602-610.
Bechert et al., "A New Method for Screening Anti-Infective Biomaterials", Nature Medicine. 6(8):1053-1056(2000).
Cheong et al., "Peritoneal healing and adhesion formation/reformation", Human Reproduction Update. 7(6):556-566 (2001).
Carbonell et al., "The susceptibility of prosthetic biomaterials to infection", Surgical Endoscopy. 19:430-435(2005) (abstract).
Kuijer et al., "Assessing infection risk in implanted tissue-engineered devices", Biomaterials. 28:5148-5154(2007).
Arciola et al., "Strong biofilm production, antibiotic multi-resistance and high geIE expression in epidemic clones of Enterococcus faecalis from orthopaedic implant infections", Biomaterials. 29:580-586(2008) (abstract).
Zheng et al., "Fatty acid synthesis is a target for antibacterial activity of unsaturated fatty acids", FEBS Letters, Elsevier, Amsterdam, NL, vol. 579, No. 23, Sep. 26, 2005, pp. 5157-5162.
Lee, Ji-Young et al., "Antimicrobial Synergistic Effect of Linolenic Acid and Monoglyceride against Bacillus cereus and *Staphylococcus aureus*", Journal of Agricultural and Food Chemistry, vol. 50, No. 7, Mar. 1, 2002, pp. 2193-2199.
Larsen, D. et al.., "Effect of cooking method on the fatty acid profile of New Zealand King Salmon (*Oncorhynchus tshawytscha*)" Food Chemistry 119 (2010) 785-790 (Year: 2010).
Steiner, M. et al. "Effect of Local Processing Methods (Cooking, Frying and Smoking) on Three Fish Species from Ghana: Part I. Proximate Composition, Fatty Acids, Minerals, Trace Elements and Vitamins" Food Chemistry 40 (1991) 309-321 (Year: 1991).

(56) References Cited

OTHER PUBLICATIONS

Gruger, Jr. E.H. Fatty Acid Composition. NMFS Scientific Publications by BOFC Fisheries. (http://spo.nmfs.noaa.gov/Circulars/CIRC276.pdf) 1967, pp. 1-30 (Year: 1967).
"Scientific Opinion on Fish Oil for Human consumption. Food Hygiene, including Rancidity", EFSA Journal—pp. 1-48, vol. 8, (2010).
"Gas Chromatography Theory"—updated Apr. 1, 2016—http://www.chem.ucia.edu/%7Ebacher/Genera1/30BL/gc/theory.html.
Steven J. Lehotay et al., "Application of Gas Chromatography in Food Analysis", Trends in Analytical Chemistry—pp. 686-697, vol. 21, (2002).
Edible Oils. (http://www.chempro.in/fattyacid.htm) accessed Apr. 14, 2014.
Malayoglu et al. "Dietary vitamin E (α-tocopheryl acetate) and organic selenium supplementation: performance and antioxidant status of broilers fed n-3 PUFA-enriched feeds" South African Journal of Animal Science 2009, 39 (4), pp. 274-285 (Year: 2009).
Therapeutic definition (http://www.thefreedictionary.com/therapeutic) accessed Apr. 29, 2016.
Viscosity (http://www.vp-scientific.com/pdfs/www.liquidcontrol.com_eToolbox_viscosity.pdf) accessed 6 Jan. 2017, p. 1-4.
Babaev, Vladimir R., et al., Macrophage Lipoprotein Lipase Promotes Foam Cell Formation and Atherosclerosis in Vivo, 103 The Journal of Clinical Investigation, 1999, 1697-1705.
Non-Final Office Action for U.S. Appl. No. 11/237,264 dated Jul. 3, 2013.
Non-Final Office Action for U.S. Appl. No. 13/593,656 dated Jul. 15, 2013.
Notice of Allowance for U.S. Appl. No. 11/525,390, dated Oct. 4, 2012.
Advisory Action for U.S. Appl. No. 12/581,582, dated Nov. 14, 2012.
Notice of Allowance for U.S. Appl. No. 11/525,390, dated Nov. 20, 2012.
Non-Final Office Action for U.S. Appl. No. 13/404,487, dated Dec. 20, 2012.
Non-Final Office Action for U.S. Appl. No. 13/184,512, dated Jan. 31, 2013.
Non-Final Office Action for U.S. Appl. No. 11/978,840, dated Feb. 19, 2013.
Non-Final Office Action for U.S. Appl. No. 13/682,991, dated Mar. 18, 2013.
Notice of Allowance for U.S. Appl. No. 13/404,487, dated Apr. 2, 2013.
Non-Final Office Action for U.S. Appl. No. 11/236,943, dated Apr. 22, 2013.
Final Office Action for U.S. Appl. No. 12/182,261, dated Apr. 30, 2012.
Final Office Action for U.S. Appl. No. 12/401,243, dated Jun. 11, 2012.
Notice of Allowance for U.S. Appl. No. 12/182,261, dated Jul. 23, 2012.
Notice of Allowance for U.S. Appl. No. 11/236,908, dated May 11, 2012.
Advisory Action for U.S. Appl. No. 12/401,243, dated Aug. 27, 2012.
Final Office Action for U.S. Appl. No. 12/581,582 dated Aug. 29, 2012.
Non-Final Office Action for U.S. Appl. No. 12/581,582 dated Mar. 14, 2012.
Final Office Action for U.S. Appl. No. 12/182,165 dated Apr. 6, 2012.
Final Office Action for U.S. Appl. No. 11/701,799 dated Feb. 13, 2012.
International Search Report for International Application PCT/US05/034601, dated Apr. 10, 2006.
International Search Report for International Application PCT/US05/034610, dated Mar. 16, 2006.
International Search Report for International Application PCT/US05/034614, dated Aug. 29, 2006.
International Search Report for International Application PCT/US05/034615, dated May 16, 2006.
International Search Report for International Application PCT/US05/034678, dated Aug. 28, 2006.
International Search Report for International Application PCT/US05/034681, dated Jul. 26, 2006.
International Search Report for International Application PCT/US05/034682, dated Jul. 20, 2006.
International Search Report for International Application PCT/US05/034836, dated Jul. 6, 2006.
International Search Report for International Application PCT/US06/037184, dated Feb. 22, 2007.
International Preliminary Report on Patentability for International Application PCT/US06/040753, dated Oct. 3, 2008.
International Search Report for International Application PCT/US06/040753, dated Sep. 24, 2007.
International Search Report for International Application PCT/US07/019978, dated May 7, 2009.
International Search Report for International Application PCT/US07/022860, dated Apr. 22, 2009.
International Search Report for International Application PCT/US07/022944, dated Apr. 8, 2009.
International Search Report for International Application PCT/US08/000565, dated May 4, 2009.
International Preliminary Examination Report for International Application PCT/US08/071547 ,dated Aug. 26, 2010.
International Search Report for International Application PCT/US08/071547, dated Oct. 22, 2008.
International Preliminary Report on Patentability for International Application PCT/US08/071565, dated Aug. 27, 2009.
International Search Report for International Application PCT/US08/071565, dated Nov. 10, 2008.
International Search Report for International Application PCT/US08/085386, dated Feb. 4, 2009.
International Search Report for International Application PCT/US09/037364, dated Aug. 27, 2009.
International Search Report for International Application PCT/US10/026521, dated Jun. 23, 2010.
International Search Report for International Application PCT/US10/052899, dated Jan. 10, 2011.
Non-final Office Action for U.S. Appl. No. 11/236,908 dated Mar. 25, 2009.
Non-final Office Action for U.S. Appl. No. 11/236,908 dated May 17, 2011.
Final Office Action for U.S. Appl. No. 11/236,908 dated Aug. 24, 2009.
Final Office Action for U.S. Appl. No. 11/236,943 dated Dec. 23, 2009.
Non-Final Office Action for U.S. Appl. No. 11/236,943 dated Mar. 5, 2009.
Non-final Office Action for U.S. Appl. No. 11/236,977 dated Aug. 3, 2009.
Final Office Action for U.S. Appl. No. 11/237,263 dated Jul. 7, 2010.
Non-final Office Action for U.S. Appl. No. 11/237,263 dated Oct. 7, 2009.
Final Office Action for U.S. Appl. No. 11/237,264 dated Jun. 2, 2010.
Non-final Office Action for U.S. Appl. No. 11/237,264 dated Oct. 5, 2009.
Final Office Action for U.S. Appl. No. 11/701,799 dated Nov. 23, 2010.
Non-final Office Action for U.S. Appl. No. 11/238,532, dated Mar. 30, 2009.
Final Office Action for U.S. Appl. No. 11/238,532 dated Sep. 9, 2009.
Final Office Action for U.S. Appl. No. 11/238,554 dated May 12, 2010.
Non-final Office Action for U.S. Appl. No. 11/238,554 dated Oct. 9, 2009.

(56) References Cited

OTHER PUBLICATIONS

Schwartz et al., "Restenosis and the Proportional Neointimal Response to Coronary Artery Injury: Results in a Porcine Model," J. Am. Coll. Cardiol., 1992, vol. 19, pp. 267-274.
PILZ and MARZ 2008, Free fatty acids as a cardiovascular risk factor. Clin Chem Lab Med, vol. 46, No. 4, pp. 429-434.
Sigma-Aldrich, Polyhydroxy compounds webpage, captured May 28, 2009.
Wanasundara et al., "Effect of processing on constituents and oxidative stability of marine oils," Journal of Food Lipids, 1998, vol. 5, pp. 29-41.
Supplementary European Search Report for Application No. 05 80 2894, dated Jul. 27, 2011.
Supplementary European Search Report for Application No. 05 800 844, dated Aug. 19, 2011.
International Preliminary Report on Patentability for Application No. PCT/US08/71565, dated Apr. 5, 2010.
Supplementary European Search Report for EP Application No. 08782511, dated Apr. 23, 2013.
Advisory Action of U.S. Appl. No. 11/238,554, dated Jul. 10, 2009.
Notice of Allowance of U.S. Appl. No. 11/238,554, dated Apr. 28, 2011.
Non-Final Office Action of U.S. Appl. No. 13/185,135, dated Jan. 25, 2011.
Non-Final Office Action of U.S. Appl. No. 12/182,165, dated Jun. 24, 2013.
Sweetman, Sean C., "Martindale: The complete drug reference," 33rd ed., 2002, Pharmaceutical Press, pp. 1-90.
Drugs.com "Drug Index a to Z," retrieved on Apr. 1, 2013, pp. 1-4.
Garner, Brian A., "A Dictionary of Modern Legal Usage," 2nd ed., 1987, pp. 389-390 and 713-717.
Pearlman, Daniel D. & Paul R., "Guide to Rapid Revision," 3rd ed., 1982, Bobbs-Merrill Educational Publishing, pp. 25-27.
Canter, Sheryl, "Chemistry of Cast Iron Seasoning: A Science-Based How-To," retrieved from sherylcanter.com on Apr. 5, 2013, pp. 1-5.
O'Neil, Maryadelle J. et al., The Merck Index—An Encyclopedia of Chemicals, Drugs, and Biologicals, 14th ed., 2006, entries for "Calcium Carbonate", "Cyclosporins", "Prussian Blue", and "Rapamycin", pp. 1-12.
EP Office Action for EP Application No. 07838216.5, dated Feb. 11, 2010.
Kugel, et al., "Minimally invasive, Nonlaparoscopic, Preperitoneal, and Sutureless, Inguinal Herniorraphy," The American Journal of Surgery, 1999, vol. 178, pp. 298-302.
Lichtenstein, et al., "Repair of Recurrent Ventral Hernias by an Internal Binder," The American Journal of Surgery, 1976, vol. 132, pp. 121-125.
Moreno-Egea, "Laparoscopic repair of Ventral and Incisional Hernias Using a new Composite Mesh (Parletex)," Surgical Laparoscopy, Endoscopy & Percutaneous Techniques, 2001, vol. 11, No. 2, pp. 103-106.
"Sharper Curve, Stronger Egg", Inside Science, printed Jan. 21, 2016, http://www.insidescience.org/content/sharper-curve-stronger-egg/779, 6 pages.
Moreno et al., J. Agric. Food Chem., 2003, vol. 51, pp. 2216-2221.
CRC Handbook of Chemistry and Physics, 89th Edition, 2008-2009, Composition and Properties of Common Oils and Fats, pp. 7-9 to 7-13.
Ali, Handbook of Industrial Chemistry: Organic Chemicals, Chapter 4, Edible Fats, Oils and Waxes, 1994, pp. 85-121.
Rietjens et al., "The pro-oxidant chemistry of the natural antioxidants vitamin C, vitamin E, carotenoids, and flavonids," Environmental Toxicology and Pharmacology, 2002, vol. 11, pp. 321-333.
European Communication for Application No. 07112611.4-2107, dated Nov. 30, 2007.
Clauss, Wolfram et al., "No Difference Among Modern Contrast Media's Effect on Neointimal Proliferation and Restenosis After Coronary Stenting in Pigs," Investigative Reporting; 2004.
Nagao et al., "Conjugated Fatty Acids in Food and Their Health Benefits," 2005, The Society for Biotechnology, Japan, Journal of Bioscience and Bioengineering, vol. 100, No. 2, pp. 152-157.
Goodnight et al., "Polyunsaturated Fatty Acids, Hyperlipidemia, and Thrombosis," 1982, American Heart Association, Journal of the American Heart Association, vol. 2, No. 2, pp. 87-113.
Bard FDA 510K Approval (Jan. 2001).
Bard Internet Publication (Apr. 2001).
Bard FDA 510K Approval (Jul. 2002).
Bellon et al., "Evaluation of a New Composite Prosthesis (PL-PU99) for the Repair of Abdominal Wall Defects in Terms of Behavior at the Peritoneal Interface," World Journal of Surgery, 26: 661-666 (2002).
Bendavid et al., "A Femoral 'Umbrella' for Femoral Hernial Repair Surgery," Gynecology and Obstetrics, 165: 153-156 (1987).
Bendavid et al., "New Techniques in Hernia Repair," World Journal of Surgery, 13: 522-531 (1989).
Greenawalt et al., "Evaluation of Sepramesh Biosurgical Composite in a Rabbit Hernia Repair Model," Journal of Surgical Research, 94: 92-98 (2000).
Helfrich et al., "Abdominal Wall Hernia Repair: Use of the Gianturco-Helfrich-Eberhach Hernia Mesh," Journal of Laparoendoscopic Surgery, 5(2): 91-96 (1995).
Hydrogenated Castor Oil, at http://www.acme-hardesty.com/product/hydrogenated-castor-oil/ (downloaded Jun. 2, 2017), which corresponds to "Exhibit B1."
Hawley's Condensed Chemical Dictionary—pp. 425 and 426 (2001), which corresponds to "Exhibit A1."
Hoefler, Andrew C., "Sodium Carboxymethyl Cellulose: Chemistry, Functionality, and Applications", Hercules Incorporated, http://www.herc.com/foodgums/index.htm, 15 pages.
Hercules Inc./Aqualon Div. CMC Quality Specifiction, Oct. 19, 2001 (Revised Sep. 2, 2008), 1 page.
Aqualon: Sodium Carboxymethylcellulose: Physical and Chemical Properties, Hercules Incorporated, 1999, 30 pages.
Fei, Bin, et al., "Hydrogel of Biodegradable Cellulose Derivatives. I. Radiation-Induced Crosslinking of CMC", Journal of Applied Polymer Science, 2000, vol. 78, pp. 278-283.
Shakhashiri, Chemical of the week Fats and Oils, at www.scifun.org (last revised Jan. 30, 2008) 2 pages.
"What are hydrogenated fats?" at http://www.whfoods.com/genpage.php?tname=george&dbid=10 (downloaded Dec. 19, 2017), 3 pages.
Sigma reference 2007.
Savolainen et al. "Evaluation of controlled-release polar lipid microparticles" International Journal of Pharmaceutics 2002 244:151-161.
Nair et al. "Antibacterial Effect of Caprylic Acid and Monocaprylin on Major Bacterial Mastitis Pathogens" Journal of Dairy Science 2005 88:3488-3495.
Office Action issued in CN Application No. 201610998395.8 dated Oct. 22, 2020, 13 pages.
Office Action issued in EP Application No. 10825447.5 dated Feb. 20, 2020, 4 pages.
Office Action issued in U.S. Appl. No. 16/165,628 dated Dec. 1, 2020, 15 pages.
Extended European Search Report issued in EP Application No. 18000936.7 dated Jan. 7, 2020, 9 pages.
Non-Final Office Action issued in U.S. Appl. No. 16/213,823 dated Feb. 14, 2020, 14 pages.
Van Den Berg et al., Chemical changes in curing and ageing oil paints, ICOM Committee for Conservation, 1999, 248-253, vol. 1.
Office Action issued in CN Application No. 201610998395.8 dated Mar. 22, 2021, 15 pages.

* cited by examiner

TISSUE-SEPARATING FATTY ACID ADHESION BARRIER

RELATED APPLICATIONS

The present application is a divisional of U.S. patent application Ser. No. 15/001,585, which was filed on Jan. 20, 2016 (now U.S. Pat. No. 9,844,611), which is a divisional application of U.S. patent application Ser. No. 12/581,582, which was filed on Oct. 19, 2009 (now U.S. Pat. No. 9,278,161), and which is a continuation-in-part of the following: United States patent applications: U.S. patent application Ser. No. 11/237,420 entitled "Barrier Layer," filed on Sep. 28, 2005 (now U.S. Pat. No. 9,801,913); U.S. patent application Ser. No. 11/237,264 entitled "A Stand-Alone Film and Methods for Making the Same," filed on Sep. 28, 2005 (now U.S. Pat. No. 8,795,703); U.S. patent application Ser. No. 11/978,840 entitled "Coated Surgical Mesh," filed on Oct. 30, 2007 (now U.S. Pat. No. 8,574,627); and U.S. patent application Ser. No. 12/401,243 entitled "Fatty-Acid Based Particles," filed on Mar. 10, 2009 (now U.S. Pat. No. 9,427,423). The contents of the aforementioned patent applications are incorporated herein by reference.

FIELD OF THE INVENTION

The present invention generally relates to a tissue-separating adhesion barrier.

BACKGROUND

Medical films are often used in surgical settings as a physical barrier to separate certain organs from adjacent tissues and medical devices following surgical intervention or blunt dissection to help minimize adhesion formation post-surgery. For example, SEPRAFILM® (a film composed of chemically modified sugars), a product of Genzyme Corporation of Cambridge, Mass., is used in abdominal or pelvic surgeries as an implantable treatment intended to reduce the incidence, extent, and severity of postoperative adhesion formation between different tissues and organs and implantable medical devices such as soft tissue support membranes and mesh, or combinations of non-absorbable materials and meshes.

One example of a medical film is described in U.S. Pat. No. 5,017,229. The film of the '229 patent is formed from a water insoluble, gel that includes the reaction product of hyaluronic acid ("HA"), a polyanionic polysaccharide, and an activating agent. The gel described in the '229 patent can be provided in the form of an adhesion prevention composition, such as a membrane or composition suitable for incorporation into a syringe. The gel is formed into a film by being cast into a sheet form, extruded, compressed, or allowed to dehydrate in a flat sheet. When modified with polysaccharide, the biodegradable film forms the above-described SEPRAFILM® adhesion-limiting or adhesion-barrier product made commercially available as a dehydrated bio-dissolvable single layer sheet.

Implantable medical films may be placed at a target site, for example, between two tissues, during surgery. In order to prevent or limit postoperative adhesion formation, the film should remain at the target site for a requisite period of time. For example, some sources have noted that barrier functionality is required between 3 days and 10 days post-surgery (see, Peritoneal Surgery by Gere. S. DiZerega, Alan H. DeCherney, Published by Springer, 2000, page 21). In order to achieve this barrier functionality, a biodegradable film should remain in place at the target site and it should be absorbed by the body for a sufficient period of time to provide barrier functionality post surgery when adhesions form.

However, conventional medical films are resorbed into the body too quickly to provide effective barrier functionality during the time in which postoperative adhesion formation typically occurs. For example, many cross-linked carboxymethylcellulose ("CMC") based films may be absorbed in-vivo within 7 days.

SUMMARY

As described in more detail below, a fatty-acid based film, such as a film made of fish oil, constructed with fixating materials, such as carboxymethylcellulose ("CMC") or Na-CMC, may be provided to fixate the film and prevent migration of the film. Despite inflammatory characteristics of CMC and the rapid resorbtion characteristics of CMC and Na-CMC, the adhesion barrier is well-tolerated by the body, is non-inflammatory, does not migrate from a target site, and does not require cross-linking of the CMC. The adhesion barrier of the present invention effectively delays resorbtion to an acceptable post implantation duration (e.g., greater than 7 days). The combination of a fatty-acid based film with a fixating material such as CMC or Na-CMC results in an unexpected synergistic effect. Specifically, non-cross-linked CMC in the presence of the fatty-acid based film does not absorb into the body as quickly as cross-linked CMC that is not in the presence of a fatty acid. As a result, the fixating portion of the adhesion barrier is absorbed into the body at a much slower rate than other CMC-based films, so that barrier functionality is provided over the time period that adhesions are likely to form.

In some exemplary embodiments of the invention, the adhesion barrier is in the form of an emulsion. The emulsion may include fatty-acid based particles immersed in an emulsion base. The fatty-acid based particles may be formed by fragmenting a fatty-acid derived biomaterial associated with a cryogenic liquid. The emulsion base may include a mixture of a fixating material, such as CMC, with an aqueous-based solution, such as (but not limited to) water, saline, or Ringer's lactate solution.

Exemplary embodiments of the present invention provide adhesion barriers and methods for formulating the adhesion barriers. In accordance with one exemplary embodiment of the present invention, the adhesion barrier takes the form of a fatty acid based film composition. The adhesion barrier includes a fatty acid based film derived from a cross-linked fatty acid-derived biomaterial and a tissue fixating coating formed from a material surrounding the fatty acid based film. The tissue fixating coating may be applied by any means known in the art.

In accordance with aspects of the present invention, the fatty acid-derived biomaterial is an omega-3 fatty acid. The fatty acid-derived biomaterial may, or may not be, cross-linked. The fatty acid-derived biomaterial may contain at least one lipid or omega-3 fatty acid; for example, the fatty acid-derived biomaterial may be a fish oil. The fish oil may further comprise vitamin E.

In accordance with one exemplary embodiment, the coherent material may be a polyanionic polysaccharide, such as carboxymethylcellulose (CMC). In accordance with another exemplary embodiment, the coherent material comprises a salt of CMC, such as sodium carboxymethylcellulose (Na-CMC).

In accordance with further aspects of the present invention, the fatty acid-derived biomaterial may reduce inflammation associated with the fixating material. In some embodiments, the adhesion barrier does not migrate from a surgical site of placement, while in further embodiments, the adhesion barrier has a residence time that is sufficient to prevent post-surgical adhesions.

BRIEF DESCRIPTION OF THE DRAWINGS

The foregoing and other aspects, embodiments, objects, features and advantages of the invention can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the invention.

DETAILED DESCRIPTION

Figure 1:
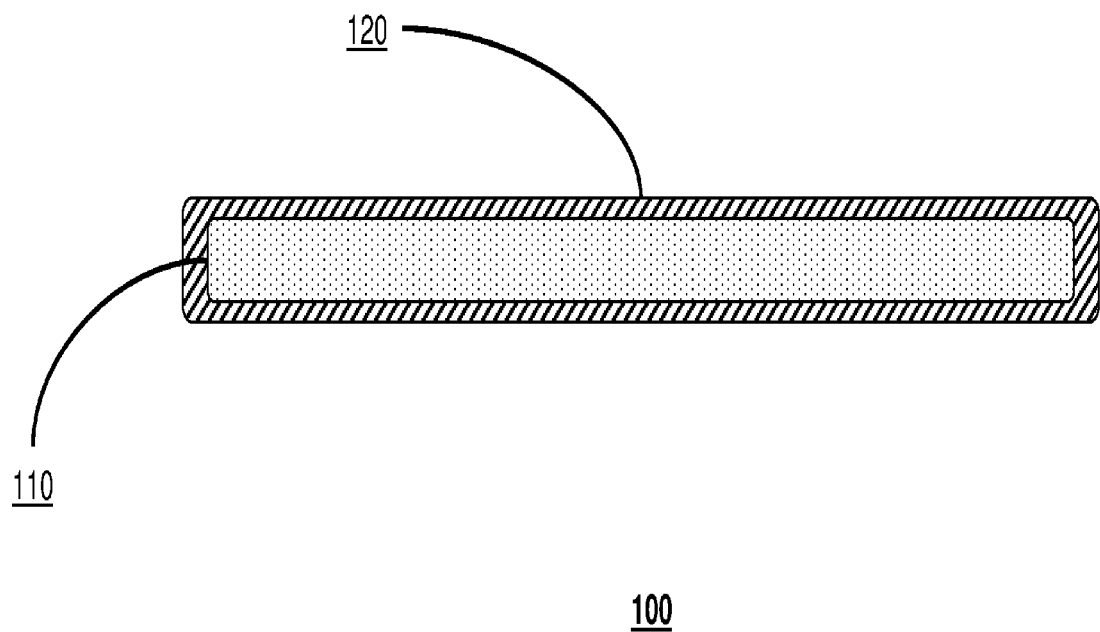
FIG. 1 depicts an adhesion barrier in accordance with one example embodiment of the present invention.

Exemplary aspects and embodiments of the present invention provide adhesion barriers formed from fatty acid-based films or fatty acid-based particles. The adhesion barriers have the fixating properties of materials, such as CMC-based films, with an additional unexpected synergistic effect, which substantially slows the rate at which the tissue fixating portion of the adhesion barrier is absorbed without requiring crosslinking of the CMC component.

Conventional Films

In some conventional products, hydrophilic tissue fixating components such as poly(ethylene glycol), poly(ethylene oxide), poly(HEMA), poly(N-vinyl pyrrolidone), poly (acrylic acid), carboxymethyl cellulose (CMC), chitosan, etc. are used to provide fixation of the film. This fixation can address the problem of film mobility or migration. However, these hydrophilic materials may exhibit appreciable foreign body reaction and inflammation, which are undesirable characteristics (see, e.g. European Patent Application EP20020080404).

Further, manufacturing these conventional tissue fixating components poses additional challenges. Specifically, the above tissue fixating components must be chemically cross-linked via functional end group modification, or by the use of chemical crosslinking agents, to provide suitable mechanical integrity for handling and insolubility in a wet environment. The use of chemical crosslinkers such as gluteraldehyde or aziridines requires the additional step of removing the excess crosslinking agents by washing or soaking, as these compounds are often less biocompatible than the desired hydrogel materials. These additional steps add to the expense and difficulty of the manufacturing process.

As noted above, films may be made of a polyanionic polysaccharide and hyaluronic acid. One preferred polyanionic polysaccharide used to make a film described in the '229 patent is CMC. The film in the '229 patent is formed with HA and CMC ("HA/CMC"). However, it has been noted that the method for preparing this type of film can be problematic because of the procedure for removing biologically toxic materials generated in the preparation (see, e.g., U.S. Patent Application Publication No. 2003/0124087). The '087 application notes that the hydration process in an HA/CMC preparation may cause difficulties in treatment and operation.

One alternative to HA/CMC is sodium carboxymethyl-cellulose ("Na-CMC"). While Na-CMC is effective as an anti-adhesion agent, it is difficult to apply Na-CMC as an anti-adhesion barrier because it is absorbed in the body too fast to be effective as an adhesion barrier. Fast absorption of a CMC-based film into the body is problematic, because the film is resorbed before it can act as an effective adhesion barrier. For example, HA/CMC films can be absorbed in 7 days, while, as noted above, barrier functionality may be required between 3 days and 10 days post-surgery, and in some instances up to 8 weeks of barrier functionality is necessary.

Further, films made from salts of CMC, such as Na-CMC, can be difficult or problematic to produce. Producing these films may require immobilization of the CMC or stabilization by cross-linking, because the Na and CMC readily dissociate in aqueous media, allowing the CMC to dissolve. Cross-linking is the process of chemically joining two or more molecules with a chemical bond. Cross-linking of CMC can be accomplished, for example, by irradiating the CMC (see, e.g., Fei et al., Hydrogel of Biodegradable Cellulose Derivative. I. Radiation-Induced Crosslinking of CMC, Journal of Applied Polymer Science, vol. 78, pp. 278-283 (2000)).

Without immobilization or stabilization of the CMC by cross-linking, the transition from solid to liquid significantly reduces the ability of Na-CMC films to provide effective barrier protection. Cross-linking CMC results in additional problems. Radiation-induced cross-linking of unmodified CMC requires the presence of a medium such as water to mobilize the macromolecules and allow for assembly. Solid phase irradiation of CMC results in degradation of the material by scission of the glycosidic bond.

Cross-linked CMC films also have the limit of being quickly resorbed in-vivo, i.e. within 7 days. In addition, CMC films are known to cause inflammation, and may lack adhesiveness and affinity (see, e.g., '087 application at paragraphs [0009]-[0013]).

Exemplary Embodiments

In contrast to conventional adhesion barriers, embodiments of the present invention provide an adhesion barrier that resides at a target site for a sufficient time to provide barrier functionality, does not require that the CMC component be cross-linked, and does not provoke a significant inflammatory response. In accordance with exemplary embodiments of the present invention, fatty acid-based films or fatty acid-based particles composed of fatty acid-derived biomaterials are used as a resorbable tissue-separating adhesion barrier material. Omega-3 and omega-6 fatty acids are examples of fatty acids that may be obtained from, for example, fish oil. Omega-3 fatty acids include eicosapentaenoic acid (EPA), docosahexanoic acid (DHA), and alpha-linolenic acid (ALA).

Fatty acid-based barriers composed of fatty acid-derived biomaterials effectively separate adjacent tissue surfaces, are well tolerated by the body, and do not exhibit the inflammatory response typical of other resorbable and permanent implant materials. While CMC-based films adhere well to tissue, CMC-based films readily dissolve in aqueous media in about 7 days.

Combining fatty acid-based films or particles with fixating materials as described herein results in an effective anti-adhesion barrier with fixating and anti-inflammation properties. Additionally, combining these two types of materials also yields an unexpected synergistic result—specifically, an adhesion barrier formed from a combination of CMC and a fatty acid-based film or fatty acid-based particles remains at the treatment site providing barrier functionality beyond 7 days and for up to 28 days or longer, without crosslinking the CMC. This provides sufficient residence time to effectively provide post-surgery barrier functionality.

Prior to describing the aspects of the present invention, it should be noted that, as used herein, the term "biocompatible," means compatible with living tissue (e.g., not toxic or injurious). Biocompatible compounds may hydrolyze into non-inflammatory components that are subsequently bioabsorbed by surrounding tissue. Biocompatible compounds are also referred to herein as "biomaterials."

Films include substances formed by compressing a gel, or by allowing or causing a gel to dehydrate, or by curing the gel using heat and/or light in various ways. In addition, films can be chemically formed in accordance with processes known by those of ordinary skill in the art.

In addition to films, exemplary embodiments of the present invention include emulsions. An emulsion is a solution of two or more immiscible liquids. In one exemplary embodiment, the emulsion is formed from an emulsion base mixed with fatty-acid based particles. The fatty-acid based particles may be derived from a fatty-acid based film.

As used herein, a fatty-acid based material is meant to encompass any form of material that the fatty acid may take, including films and particles.

Exemplary Film Embodiments

FIG. 1 depicts an adhesion barrier 100 according to one embodiment of the present invention. The adhesion barrier 100 includes a fatty acid-based film 110. The fatty acid-based film 110 may be formed by any of the methods known in the art. In one embodiment, a crosslinked, fatty acid-derived biomaterial comprises an oil that may be natural or derived from synthetic sources and is used to form the fatty acid-based film 110. The crosslinked, fatty acid-derived biomaterial can comprise a biological oil, such as an oil containing at least one lipid or omega-3 fatty acid, including a fish oil. The biomaterial further can include vitamin E.

The adhesion barrier 100 also includes a tissue fixating coating 120 formed from an fixating material. In one embodiment, the fixating material is a polyanionic polysaccharide. In another embodiment, the fixating material comprises carboxymethylcellulose (CMC). In yet another embodiment, the fixating material comprises sodium carboxymethylcellulose (Na-CMC).

Figure 2:
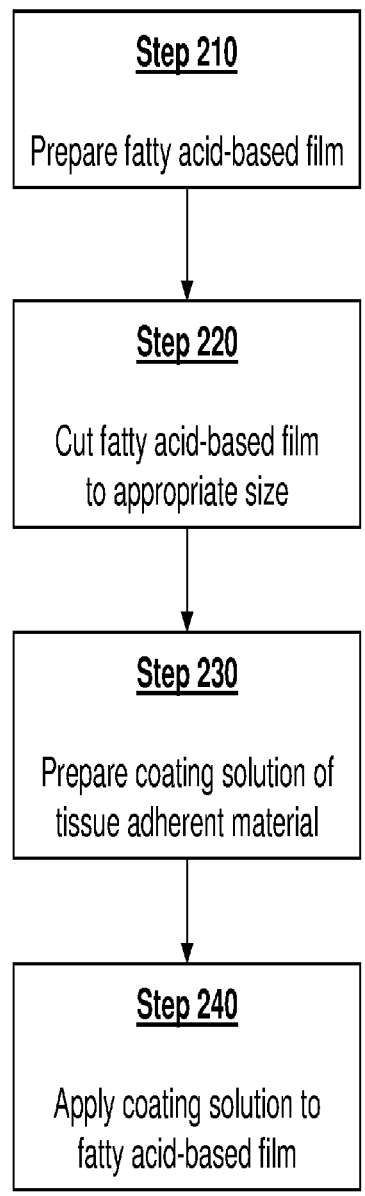
FIG. 2 is a flow chart depicting an exemplary method for fabricating an exemplary adhesion barrier in accordance with one example embodiment of the present invention.

FIG. 2 is a flow chart depicting an exemplary method for fabricating the adhesion barrier 100. At step 210, a fatty acid-based film 110 is prepared by one of the methods known in the art. For example, as described in U.S. patent application Ser. No. 11/237,420, which is incorporated herein by reference in its entirety, fish oil may be exposed to heating and/or UV irradiation to form a cross-linked, fatty acid-derived biomaterial such as a gel. The gel may further be compressed or dehydrated to form a film. One of ordinary skill in the art will appreciate that other methodologies may be utilized to form the fatty acid-based film 110, and the present invention is by no means limited to the particular methods described in the above-referenced application or patent. For example, the fatty acid-based film 110 may be prepared according to the procedure described in U.S. patent application Ser. No. 11/237,264, which is now U.S. Pat. No. 8,795,703, both of which are incorporated herein by reference in their entirety.

The oil component may also be hardened, as described in the '420 application, in addition to other known methodologies. The step of hardening can include hardening, or curing, such as by introduction of UV light, heat, or oxygen, chemical curing, or other curing or hardening method. The purpose of the hardening or curing is to transform the more liquid consistency of the oil component or oil composition into a more solid film, while still maintaining sufficient flexibility to allow bending and wrapping of the film as desired.

In some embodiments, the oil component is subjected to a surface treatment prior to coating, such as a plasma treatment.

At step 220, the fatty acid-based film 110 is optionally cut to an appropriate size. The final dimensions of the cut fatty acid-based film 110 will be dependent on the specific application.

At step 230, a coating solution of tissue fixating material is prepared. In accordance with one exemplary embodiment of the present invention, the coating solution is composed of 0.1%-5% (weight/volume) non-crosslinked high molecular weight Na-CMC with a degree of substitution of 0.65-0.85 (although degrees of substitution below 0.65 and up to a theoretical limit of 3 are also acceptable) in a water solution, such as deionized water or Sterile Water for Injection (SWFI). Optionally, the coating solution may include a plasticizing agent, such as glycerin, propylene glycol, poly ethylene glycol, triacetin citrate or triacetin.

At weight/volume concentrations higher than about 5%, the solution becomes a solid-like gel, which may be difficult to work with. Generally, most solutions with a concentration of less than 5% are physically workable, but care should be taken with the mass loading of, for example, Na-CMC on the surface of the film. If there is too little Na-CMC it will result in an adhesion barrier with insufficient tissue fixation. Low Na-CMC concentration may require many coating applications to achieve to the desired loading. In one embodiment, a weight/volume concentration of 2% is used. We have found that a minimum dry loading of 1.0 mg/cm$^2$ may be used to achieve adequate tissue fixation in-vivo.

A high molecular weight of, for example, 700,000 for Na-CMC may be used for the tissue fixating material. In separate evaluations of chitosan, the inventors have found that tissue fixation appears to increase with molecular weight.

Based on experimental observations, and not being bound by theory, the tissue fixation is due to the hydroscopicity of the coating. Because the hydroscopicity increases with increasing degrees of substitution, all practical ranges of degrees of substitution are acceptable in the present invention. A degree of substitution of between 0.65-1.2 is a range that is practical and readily available At step 240, the coating solution is applied to the fatty acid-based film 110 using any standard coating method, such as dip coating, spray coating, brushing, casting, or spin coating. At step 250, the coating is allowed to dry for a suitable amount of time, for example 2-24 hours. Alternatively, an apparatus may be used to accelerate drying through various known methods, so long as the temperature of the coating solution is not raised too high (resulting in an aqueous or gelatinous coating). For example, the film may be vacuum dried.

Figure 3:
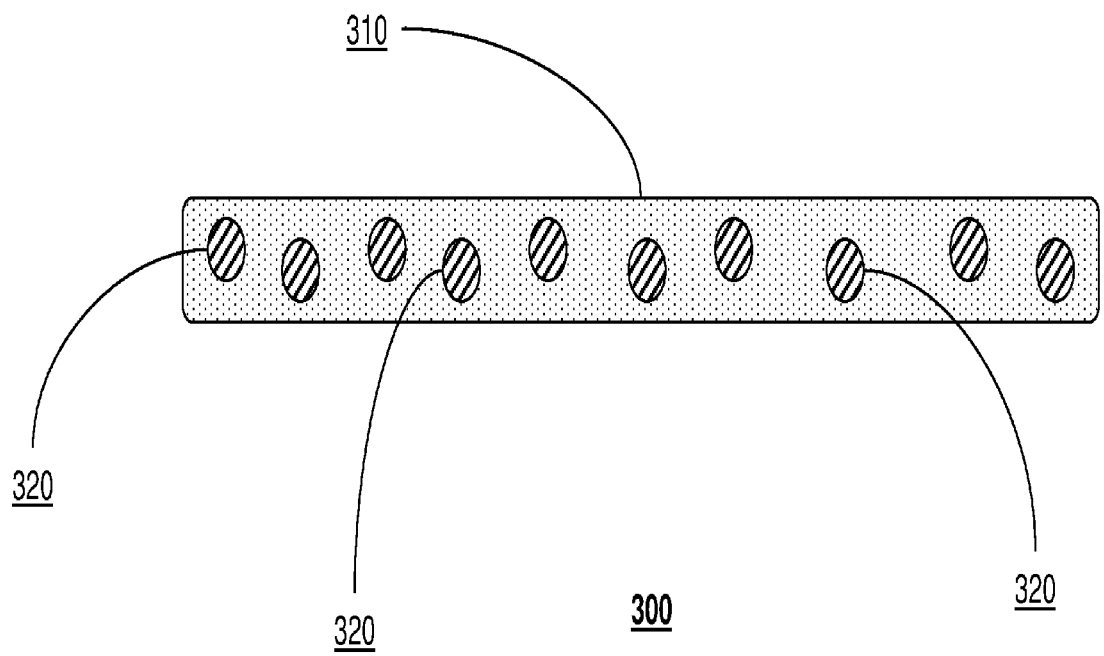
FIG. 3 depicts an adhesion barrier in accordance with one example embodiment of the present invention.

As an alternative to coating the fatty acid-based film with a fixating material, the fixating material may be introduced into the original oil or gel before it is formed into a film. An example of an adhesion barrier in accordance with such an embodiment is shown in FIG. 3. As shown, the adhesion barrier 300 is formed of a fatty acid-based film 310. The adhesion barrier 300 further includes fixating particles 320 formed from a fixating material, such as Na-CMC. Such an embodiment may be formed, for example, by a pressed particle method in which particles of a fatty acid, such as O3FA, are formed and particles of a fixating material are formed. The two types of particles are then mixed together and pressed to form an adhesion barrier. One of ordinary skill in the art will appreciate other methods for combining two materials together to form an intermixed, composite, type of material. All such methods, to the extent compatible with the materials discussed herein, are contemplated in the present invention.

Figure 4:
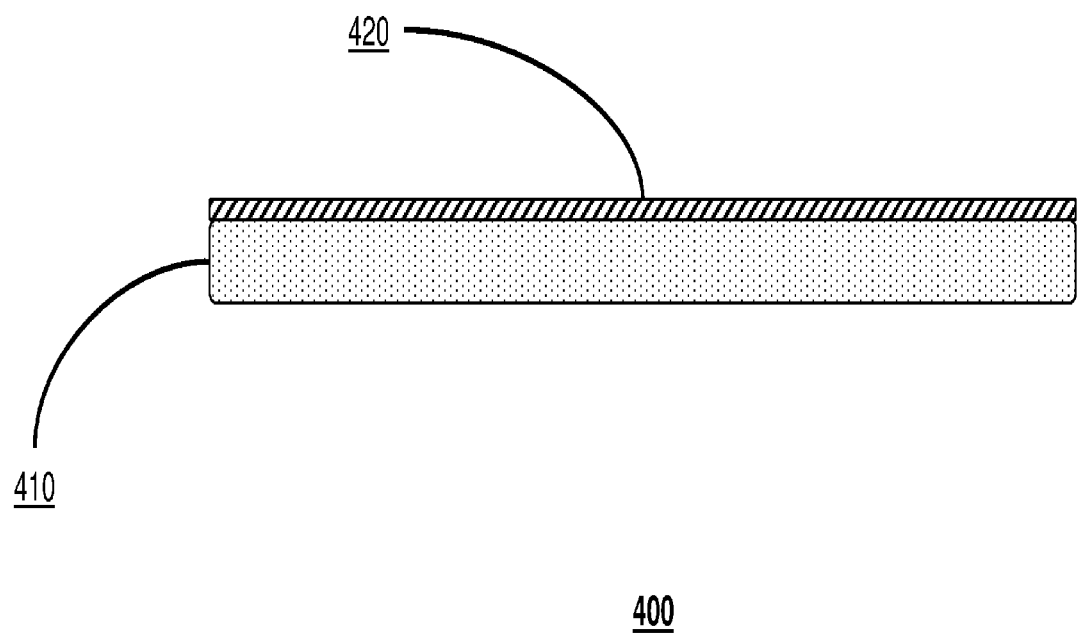
FIG. 4 depicts an adhesion barrier in accordance with one example embodiment of the present invention.

FIG. 4 depicts another alternative embodiment of the present invention. In the adhesion barrier depicted in FIG. 4, the adhesion barrier 400 is formed of a fatty acid-based film 410. The fatty acid-based film 410 is coated with an fixating coating 420 on only one side. Such an adhesion barrier may be formed, for example, by brushing or spraying the fixating coating 420 on only a single side of the fatty-acid based film 410. Other means of coating fatty-acid based film 410 on a single side will be apparent to one having ordinary skill in the art in light of the present disclosure. Alternatively, the fatty acid-based film 410 may be coated on two or more surfaces without entirely surrounding the fatty acid-based film. Accordingly, tissue fixation can be achieved on one or both sides of the fatty acid-based film.

Exemplary Emulsion Embodiments

Figure 5:
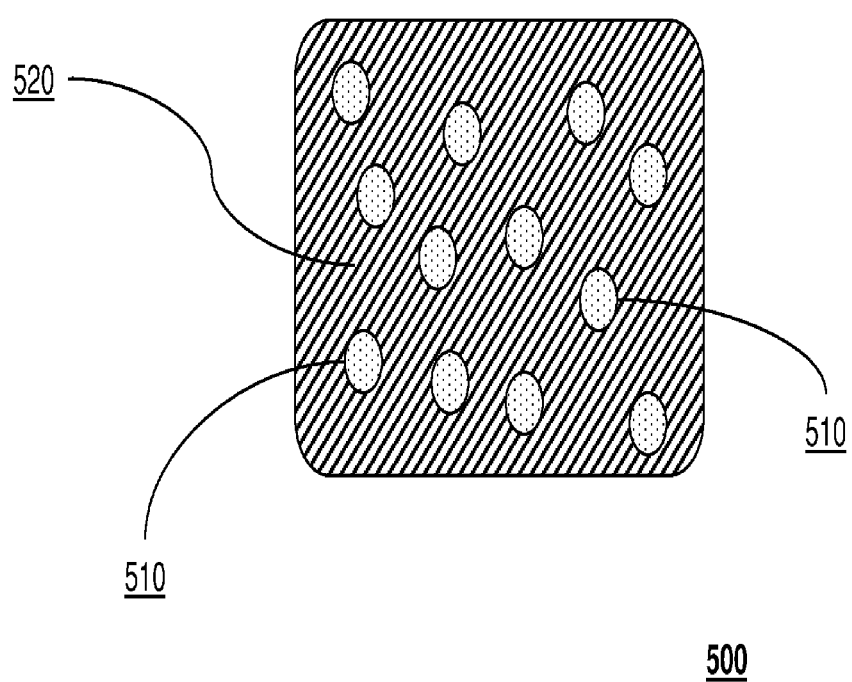
FIG. 5 depicts an adhesion barrier created as an emulsion in accordance with one example embodiment of the present invention.

FIG. 5 depicts another alternative embodiment of the present invention. The adhesion barrier 500 depicted in FIG. 5 is an emulsion of fatty-acid based particles 510 mixed with an emulsion base 520, such as a CMC and water mixture.

The fatty-acid based particles 510 may be formed by associating a cross-linked fatty acid-derived biomaterial with a cryogenic liquid and fragmenting the biomaterial/cryogenic liquid composition, such that fatty acid particles are formed. In one embodiment, the source of the cross-linked fatty acid-derived biomaterial is a fish oil, e.g., a fish oil that has been heated or exposed to UV-radiation in order to cross link some or all of the fatty acids of the fish oil.

In one embodiment, associating the cross-linked fatty acid-derived biomaterial with a cryogenic liquid includes suspending, submerging, and surrounding the cross-linked fatty acid-derived biomaterial. In another embodiment, the cryogenic liquid comprises liquid nitrogen. The cross-linked fatty acid-derived biomaterial/cryogenic liquid composition can be fragmented using one or more of grinding, shearing, shocking, shattering, granulating, pulverizing, shredding, crushing, homogenizing, sonicating, vibrating, and/or milling. The cryogenic liquid can be substantially removed by evaporation, either before fragmentation or after the particles are formed.

The cross-linked, fatty acid-derived biomaterial can comprise an oil that may be natural or derived from synthetic sources. The cross-linked, fatty acid-derived biomaterial can comprise a biological oil, such as an oil containing at least one lipid or omega-3 fatty acid, such as a fish oil. The fish oil further can include vitamin E. As described herein, the fish oil is exposed to heating and/or UV irradiation to form a cross-linked, fatty acid-derived biomaterial (e.g., gel). In one embodiment, before being associated with a cryogenic liquid, the cross-linked material is in the form of a film. In another embodiment, the film is coarsely ground prior to association with the cryogenic liquid.

When the cross-linked, fatty acid-derived biomaterial is in the form of a film, a therapeutic agent can be loaded into the film before particle formation, during particle formation, or after particle formation. In still another embodiment, the film is coated with a therapeutic agent/solvent mixture. The therapeutic agent can be dissolved in a solvent, such as methanol or ethanol, and the therapeutic agent/solvent mixture can be applied to the film, e.g., by dipping or spraying.

Once prepared, the fatty-acid based particles 510 can be soaked in a therapeutic agent dissolved in solvent, such as hexane, isopar, water, ethanol, methanol, proglyme, methylene chloride, acetonitrile, acetone, or MEK, and the solvent can be substantially removed, resulting in fatty acid particles associated with a therapeutic agent.

The therapeutic agent can be one or more of an antioxidant, anti-inflammatory agent, anti-coagulant agent, drug to alter lipid metabolism, anti-proliferative, anti-neoplastic, tissue growth stimulant, functional protein/factor delivery agent, anti-infective agent, imaging agent, anesthetic agent, chemotherapeutic agent, tissue absorption enhancer, anti-adhesion agent, germicide, analgesic, antiseptic, or pharmaceutically acceptable salts, esters, or prodrugs thereof. In particular embodiments, the therapeutic agent is selected from the group consisting of rapamycin, marcaine, Cyclosporine A (referred to herein as "CSA"), ISA 247 (referred to herein as "ISA") and rifampicin.

In one embodiment, the mean particle size of the fatty-acid based particles 510 is in the range of about 1 micron to about 50 microns, e.g., 1 micron to about 10 microns. In another embodiment, the particles have a distribution of size of about 1-20 μm (v,0.1), 21-40 μm (v,0.5), and 41-150 μm (v,0.9).

The emulsion base 520 is a liquid or aqueous-based solution which does not combine with the fatty-acid based particles 510 when mixed. In one example, the emulsion base is a CMC and water mixture. Other suitable emulsion bases include, but are not limited to, saline solutions and Ringer's lactate solution. The emulsion base may include a tissue coherent material.

Figure 6:
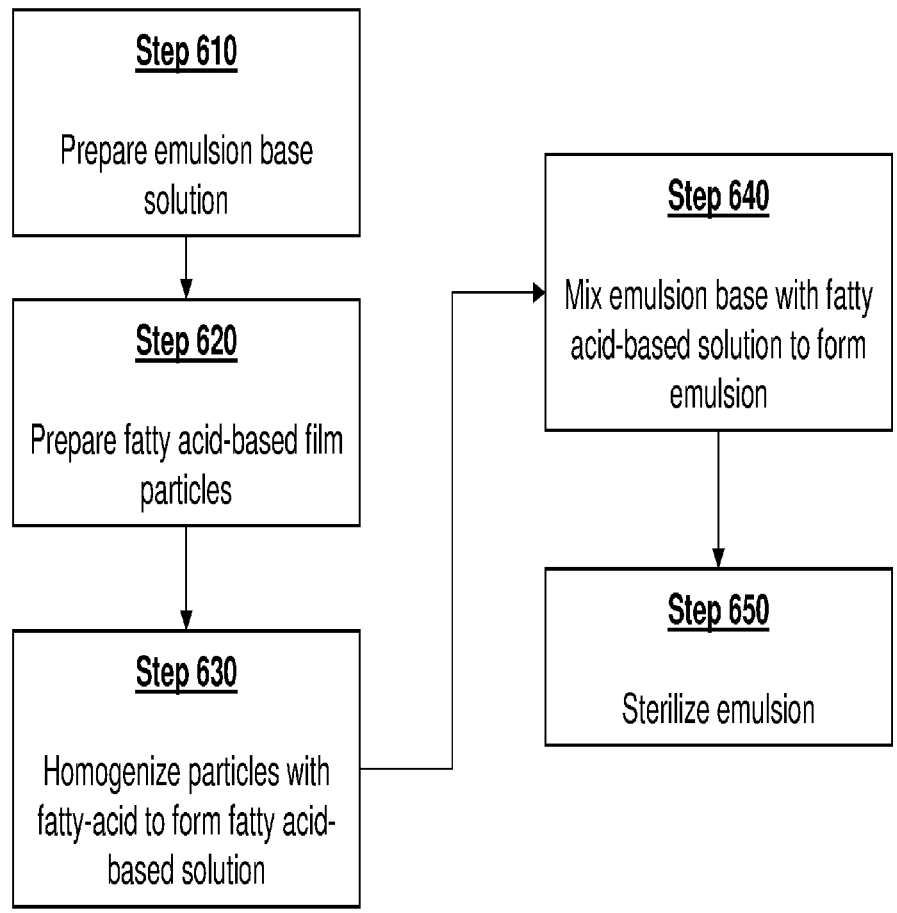
FIG. 6 is a flow chart depicting an exemplary method for fabricating an exemplary adhesion barrier as depicted in FIG. 5.

FIG. 6 is a flowchart depicting an exemplary method for creating the adhesion barrier of FIG. 5. At step 610, an emulsion base solution is prepared. In one example, an emulsion base solution comprising a CMC and water mixture (4.2% w/w) was prepared using a Silverson Homogenizer (8 kRPM) and was allowed to swell at room temperature overnight.

At step 620, fatty-acid based film particles are prepared, as described above. Specifically, the fatty-acid based particles may be formed by: (a) combining a cross-linked, fatty acid-derived biomaterial (e.g., a cross-linked fish oil) and a therapeutic agent to form a first composition; (b) submerging, surrounding, or suspending the composition in a cryogenic liquid (c) fragmenting the composition; and (d) optionally removing the dispersing media.

The dispersing media may comprise a solvent that will not dissolve the therapeutic agent or the cross-linked, fatty acid-derived biomaterial. In still another embodiment, the solvent is hexane, Isopar, water, ethanol, methanol, Proglyme, methylene chloride, acetonitrile, acetone, MEK, liquid nitrogen, and other solvents that do not fully dissolve the therapeutic agent. In another embodiment, the cross-linked, fatty acid-derived biomaterial is in the form of a film. In another embodiment, the film is coarsely ground prior to association with the therapeutic agent.

The starting materials may be fragmented into solid particles by impacting the starting materials with a rod that is magnetically actuated. For example, a Spex Certiprep Cryomill (model 6750) can be used to fragment solid materials into particles. The composition can be placed in an enclosed vial, and a rod like impactor is enclosed in the vial. The vial is maintained at cryogenic temperatures, and the rod is rapidly oscillated in the vial by means of magnets.

In one example, fish oil was partially cured then cast into a thin film 6 mil (0.006") in thickness. The thin film was UV cured for 15 minutes, heat cured in an oven at 93° C. for 24 hours, and then cooled for 24 hours. The cured fish oil films were ground with a mortar and pestle in the presence of liquid nitrogen. The thin film particles were further ground using a cryogrinder for 8 cycles. In each of the 8 cycles, the cryogrinder was on for 2 minutes at speed 15 and off for 2 minutes. The particles were stored at −20° C.

At step 630, the particles are homogenized with a fatty acid in order to form a fatty acid-based solution. In one exemplary embodiment, 1 gram of the particles was homogenized with 8 grams of fish oil using the Silverson Homogenizer (8 kRPM) until all the particles were evenly dispersed.

At step 640, the emulsion base is mixed with the fatty acid-based solution to form an emulsion. In one example, the fatty acid-based solution was mixed with 31 grams of 4.2% CMC gel (after swelling) using the Silverson Homogenizer (8 kRPM).

At step 650, the emulsion is sterilized. For example, the emulsion may be e-beam sterilized at a dose of 23 kGy.

An exemplary emulsion was prepared following steps 610-650. The resulting emulsion had a viscosity in the range of 50,000-75,000 cP.

In use, the adhesion barrier of the present invention is applied at a target site, for example a surgical site. The adhesion barrier may be applied between two areas of interest—for example, between tissues, organs, meshes, or other non-absorbable materials. The fixating properties of the adhesion barrier cause the adhesion barrier to fixate to the areas of interest so that the barrier does not migrate from the target site.

It should also be noted that the present description makes use of meshes as an example of a medical device that can be combined with the adhesion barriers of the present disclosure. However, the present disclosure is not limited to use with meshes. Instead, any number of other implantable medical devices can be combined with the adhesion barriers in accordance with the teachings of the present disclosure. Such medical devices include catheters, grafts, balloons, prosthesis, stents, other medical device implants, and the like. Furthermore, implantation refers to both temporarily implantable medical devices, as well as permanently implantable medical devices.

Figure 7A:
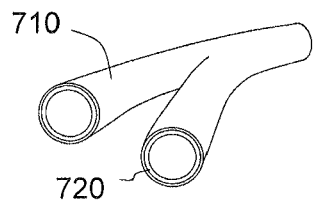
FIGS. 7A, 7B, 7C, 7D, 7E, 7F, and 7G depict exemplary embodiments of an adhesion barrier coupled with various medical devices.
Figure 7B:
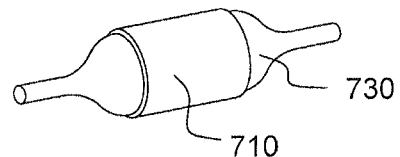
Figure 7C:
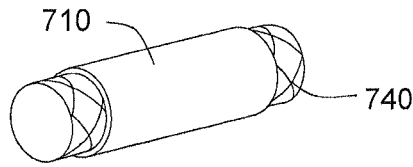
Figure 7D:
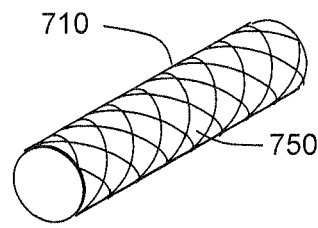
Figure 7E:
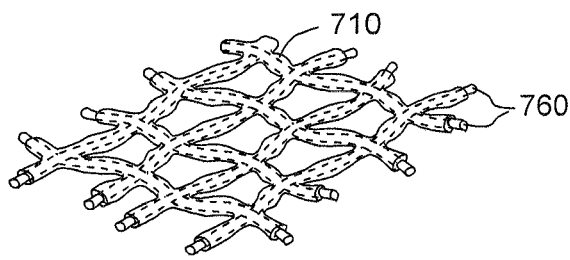
Figure 7F:
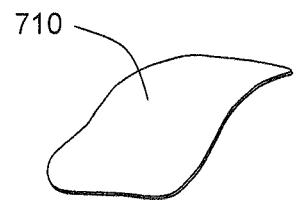
Figure 7G:
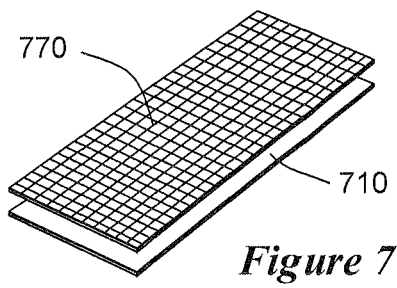

FIGS. 7A, 7B, 7C, 7D, 7E, 7F, and 7G illustrate some of the forms of medical devices mentioned above in combination with the adhesion barriers 710 of the present disclosure. FIG. 7A shows a graft 720 with the adhesion barrier 710 coupled or adhered thereto. FIG. 7B shows a catheter balloon 730 with the adhesion barrier 710 coupled or adhered thereto. FIG. 7C shows a stent 740 with the adhesion barrier 710 coupled or adhered thereto. FIG. 7D illustrates a stent 750 in accordance with one embodiment of this disclosure. The stent 750 is representative of a medical device that is suitable for having particles applied thereon to effect a therapeutic result. The stent 750 is formed of a series of interconnected struts having gaps formed there between. The stent 750 is generally cylindrically shaped. FIG. 7E illustrates a coated surgical mesh (coated with the adhesion barrier 710), represented as a biocompatible mesh structure 760, in accordance with one embodiment of the present disclosure. The biocompatible mesh structure 760 is flexible, to the extent that it can be placed in a flat, curved, or rolled configuration within a patient. The biocompatible mesh structure 760 is implantable, for both short term and long term applications. Depending on the particular formulation of the biocompatible mesh structure 760, the biocompatible mesh structure 760 will be present after implantation for a period of hours to days, or possibly months, or permanently. FIG. 7F illustrates an adhesion barrier 710 in the form of a stand alone film in accordance with one embodiment of the present disclosure. The adhesion barrier 710 is flexible, to the extent that it can be placed in a flat, curved, or rolled, configuration within a patient. The adhesion barrier 710 is implantable, for both short term and long term applications. Depending on the particular formulation of the adhesion barrier 710, the adhesion barrier 710 will be present after implantation for a period of hours to days, or possibly months. FIG. 7G illustrates the adhesion barrier 710 and a medical device in the form of a mesh 770. In the figure, the adhesion barrier 710 and mesh 770 are shown in exploded view. In instances of the mesh 770, it can be useful to have one side of the mesh support a rougher surface to encourage tissue in-growth, and the other side of the mesh with an anti-adhesion, anti-inflammatory, and/or non-inflammatory surface to prevent the mesh from injuring surrounding tissue or causing inflammation. The coupling of the adhesion barrier 710 with the mesh 770 achieves such a device. Each of the medical devices illustrated, in addition to others not specifically illustrated or discussed, can be combined with the adhesion barrier 710 using the methods described herein, or variations thereof. Accordingly, the present disclosure is not limited to the example embodiments illustrated. Rather, the embodiments illustrated are merely example implementations of the present disclosure.

Post surgery, the surgical incision is closed and the target site is allowed to heal. Under normal conditions without use of an adhesion barrier, adhesions would begin to form between the areas of interest. For example, fibrous bands may form between tissues and organs 3 to 10 days post surgery. When the adhesion barrier is present at the target site, the adhesion barrier prevents adhesions from forming. Because the adhesion barrier fixates sufficiently to the areas of interest, and because the adhesion barrier is absorbed into the body relatively slowly, the adhesion barrier is in place at the target site at the time adhesions would otherwise form.

After barrier functionality is no longer needed, the adhesion barrier is absorbed into the body.

Exemplary illustrative embodiments are described below.

Example 1: Bench Top Force of Detachment—Non Sterile Samples

A coating solution composed of 2% (w/v) non-crosslinked high molecular weight Na-CMC with a degree of substitution of 0.65 (Sigma) in deionized water was applied to 15 one inch square fatty acid-based films and allowed to dry to form adhesion barriers in accordance with embodiments of the present invention. The adhesion barriers were placed on freshly slaughtered bovine intestine that was rinsed in tap water prior to testing. The adhesion barriers were allowed to remain on the tissue for 3 minutes before testing. A Chatillon gauge was used to measure the force of detachment in the direction parallel to the plane of adhesion between the adhesion barriers and the tissue. The maximum force measured on the Chatillon gauge for each sample was collected. 15 uncoated fatty acid-based films were measured for reference. The uncoated films had a mean force of detachment of 0.08 lbf. In contrast, the coated films forming adhesion barriers in accordance with embodiments of the present invention had a mean force detachment of 0.54 lbf.

Example 2: In-Vivo Results of a Fatty Acid-CMC Film in Minimizing Tissue to Tissue Adhesions Test samples of an adhesion barrier in accordance with exemplary embodiments of the present invention were produced using the methods described above in Example 1. The CMC was not modified to enhance crosslinking and no crosslinking facilitators were employed. The test samples were implanted in a rabbit sidewall model of adhesion prevention. Samples were sterilized using an electron beam at a dose of 22.5 kGy. The cecum was fully abraded to produce punctate bleeding and a 3×5 cm section of the peritoneum was excised. This model yields dense adhesions in untreated animals. A 4×6 cm O3FA film coated with CMC was placed on the peritoneal defect with the coated side in direct contact with the sidewall. At 28 days post implant, the rabbits were sacrificed and the area of adhesions was graded.

Four rabbits were maintained as a control group with no treatment. Five rabbits were treated with the adhesion barriers. In the four control subjects, the mean area of adhesion was 100%. In the experimental subjects having the adhesion barriers, the mean area of adhesion was 8%.

As noted, no crosslinking facilitators were employed in this example. Electron beams are known to degrade previous solid CMC films which will result in faster absorption in-vivo. However, despite the use of e-beam sterilization, the results from Example 2 show that the adhesion barriers remained tissue coherent for at least 28 days.

Example 3

Crosslinking via radiation exposure is a method that can be used to increase the in-vivo residence time of aqueous CMC compositions. To evaluate the effect of radiation exposure on dry CMC films, a solution composed of 2% (w/v) Na-CMC with a degree of substitution of 0.7 (Hercules) in SWFI was diluted with SWFI in a solution:SWFI ratio of 5:2. The dilute solution was poured into a Teflon coated well plate and allowed to dry at room temperature for 24 hours, resulting in a thin solid film of CMC. The film was cut into several square pieces that were packaged separately. Several pieces were irradiated using a 10 MeV electron beam source at a dose of 22.5 kGy. Irradiated and non-irradiated samples were submerged in separate aluminum pans of deionized water and evaluated for solubility and maintenance/loss of structure. If the CMC films were crosslinked by the exposure to radiation, hydration of the films should result is some swelling with maintenance of the original square geometry. In contrast, both irradiated and non-irradiated films swelled and lost structure within about 10 minutes and were no longer detectable as solids or gels by 30 minutes, indicating that the CMC was fully mobile (not crosslinked or otherwise immobilized via chemical bonding) in both samples. The CMC solutions in the pans were allowed to evaporate over 48 hours at ambient room temperature, yielding uniformly thin solid films of CMC that conformed to the circular pan geometry at the bottom of the pan. Full and equal solubility of exposed and non-exposed CMC films is evidence that the electron beam exposure did not constructively limit the mobility of (i.e. crosslink) the CMC material.

To further evaluate the effect of radiation crosslinking on CMC in the presence of O3FA, two test samples of an adhesion barrier in accordance with exemplary embodiments of the present invention were produced using the methods described above in Example 1. Adhesion Barrier 1 was exposed to a 10 MeV electron beam source with a dose of 22.5 kGy. Adhesion Barrier 2 was not exposed to electron beam radiation. The adhesion barriers were weighed and exposed to 200 mL of deionized water, with visual evaluation at 2, 5, and 69 hours. The adhesion barriers were then vacuum dried for 2 hours at 25 mTorr. Measurements and observations are provided below in Table 1.

TABLE 1

| Sample | E-beam Exposure | Film Area [cm$^2$] | Initial Mass [mg] | Observation after 2 h in DI water | Observation after 5 h in DI water | Observation after 69 h in DI water | Final Mass [mg] | Mass/Area Lost [mg/cm$^2$] |
|---|---|---|---|---|---|---|---|---|
| 1 | Yes | 27.72 | 499.1 | Gel layer thickness of 3 mm | Gel layer thickness of 1 mm | No gel layer | 438.9 | 2.17 |
| 2 | No | 23.18 | 367.3 | Gel layer thickness of 3 mm | Gel layer thickness of 1 mm | No gel layer | 317.6 | 2.14 |

The authors had previously determined that the coating method employed yields a coating mass density of 2.28+/−0.11 mg/cm$^2$ (mean+/−1σ, n=12). Both adhesion barriers have mass losses (2.17 and 2.14 mg/cm$^2$, respectively) that support the conclusion that the coating is fully soluble in DI water, and therefore not crosslinked or otherwise immobilized. Visual observations support this conclusion.

CMC in the presence of O3FA took between 5 and 69 hours to fully dissolve in DI water, whereas CMC only films were fully dissolved in 30 minutes. The presence of O3FA appears to slow the dissolution of CMC in DI water. This is independent of irradiation with electron beam.

Example 4

A coating solution composed of 2% (w/v) Na-CMC with a degree of substitution of 0.7 (Hercules) and 1% glycerin in SWFI was prepared. The coating solution was applied to several fatty acid-based films and was allowed to dry to form adhesion barriers. The adhesion barriers exhibited excellent handling, as the coating was well plasticized. The adhesion barriers were sterilized using an electron beam at a dose of 22.5 kGy and implanted in a rabbit sidewall model of adhesions. The cecum was fully abraded to produce punctate bleeding and a 3×5 cm section of the peritoneum as excised. A 4×6 cm film coated with CMC was placed on the peritoneal defect with the coated side in direct contact with the sidewall. At 28 days post implant, the rabbits were sacrificed and the area of adhesions was graded.

Four rabbits were maintained as a control group with no treatment. Five rabbits were treated with the adhesion barriers. In the four control subjects, the mean area of adhesion was 100%. In the experimental subjects having the adhesion barriers, the mean area of adhesion was 8%.

The results show that, in this study, the addition of a plasticizing agent had no effect on the efficacy of the adhesion barriers comprising an O3FA-CMC film, as the adhesion barrier did not migrate from the site of treatment. The results of this study show that the plasticized adhesion barrier was tissue fixating for at least 28 days.

Example 5: O3FA Film with Tissue Fixating Chitosan Coating

A coating solution composed of 4% (w/v) ChitoPharm S (MW=50,000-1,000,000, Cognis) in a 1% acetic acid solution was dialyzed using a Fisherbrand regenerated cellulose dialysis tubing membrane with a molecular weight cut off of 3,500. The final coating solution pH was 6.27. The coating was applied to several 4×6 cm O3FA films and evaluated in a rabbit sidewall model of adhesion prevention. Samples were sterilized using E-beam at a dose of 22.5 kGy. The cecum was fully abraded to produce punctate bleeding and a 3×5 cm section of the peritoneum was excised. This model yields dense adhesions in untreated animals. The 4×6 cm films coated with chitosan were placed on the peritoneal defect with the coated side in direct contact with the sidewall. At 28 days post implant, the rabbits were sacrificed and the area of adhesions was graded. Results are shown in the table below.

| Group | Description | n | Mean Area of Adhesions (%) |
|---|---|---|---|
| 1 | control, no treatment | 4 | 100 |
| 2 | Chitosan Coating | 5 | 34 |

Example 6: Emulsion

An adhesion barrier in the form of an emulsion, as depicted in FIG. 5, was prepared according to the procedure described in FIG. 6. Samples of the emulsion were stored at 4° C. until being tested.

Test samples of the emulsion were examined in a rabbit sidewall model to assess adhesion prevention. The cecum was fully abraded to produce punctate bleeding and a 3×5 cm section of the peritoneum was excised. This model yields dense adhesions in untreated animals. 10 mL of the emulsion was applied to the peritoneal and sidewall injuries. At 28 days post implant, the rabbits were sacrificed and the area of adhesions was graded.

Results showed that three of the six animals tested had no adhesion formation (area=0%). The remaining three that did form adhesions had a tenacity of only 1, indicating that the adhesions were mild and easily dissectible. The average area of adhesion coverage was 28.3% and the average tenacity score was 0.5. These results contrasted that of the control, untreated animal, as detailed in the table below.

| Group | Description | n | Mean Area of Adhesions (%) | Tenacity |
|---|---|---|---|---|
| 1 | Control, no treatment | 4 | 100 | 2.75 |
| 2 | Emulsion | 6 | 28.3 | 0.5 |

Biocompatibility and In-Vivo Performance

The process of making the fatty acid-based biomaterials as described in accordance with the present invention led to some unexpected chemical processes and characteristics in view of traditional scientific reports in the literature about the oxidation of oils (J. Dubois et al. *JAOCS.* 1996, Vol. 73, No. 6, pgs 787-794. H. Ohkawa et al., Analytical Biochemistry, 1979, Vol. 95, pgs 351-358; H. H. Draper, 2000, Vol. 29, No. 11, pgs 1071-1077). Oil oxidation has traditionally been of concern for oil curing procedures due to the formation of reactive byproducts such as hydroperoxides and alpha-beta unsaturated aldehydes that are not considered to be biocompatible (H. C. Yeo et al. Methods in Enzymology. 1999, Vol. 300, pgs 70-78; S-S. Kim et al. Lipids. 1999, Vol. 34, No. 5, pgs 489-496.). However, the oxidation of fatty acids from oils and fats are normal and important in the control of biochemical processes in-vivo. For example, the regulation of certain biochemical pathways, such as to promote or reduce inflammation, is controlled by different lipid oxidation products (V. N. Bochkov and N. Leitinger. J. Mol. Med. 2003; Vol. 81, pgs 613-626). Additionally, omega-3 fatty acids are known to be important for human health and specifically EPA and DHA have anti-inflammatory properties in-vivo. However, EPA and DHA are not anti-inflammatory themselves, but it is the oxidative byproducts they are biochemically converted into that produce anti-inflammatory effects in-vivo (V. N. Bochkov and N. Leitinger, 2003; L. J. Roberts II et al. The Journal of Biological Chemistry. 1998; Vol. 273, No. 22, pgs 13605-13612.). Thus, although there are certain oil oxidation products that are not biocompatible, there are also several others that have positive biochemical properties in-vivo (V. N. Bochkov and N. Leitinger, 2003; F. M. Sacks and H. Campos. J Clin Endocrinol Metab. 2006; Vol. 91, No. 2, pgs 398-400; A. Mishra et al. Arterioscler Thromb Vasc Biol. 2004; pgs 1621-1627.). Thus, by selecting the appropriate process conditions, an oil-derived cross-linked hydrophobic biomaterial can be created and controlled using oil oxidation chemistry with a final chemical profile that will have a favorable biological performance in-vivo.

The process of making an oil-derived hydrophobic non-polymeric biomaterial in accordance with the present invention leads to a final chemical profile that is biocompatible, minimizes adhesion formation, acts as a tissue separating barrier, and is non-inflammatory with respect to the material chemistry and the products produced upon hydrolysis and absorption by the body in-vivo. These properties are due to several unique characteristics of the fatty acid-derived biomaterials in embodiments of the present invention.

One aspect of the present invention is that no toxic, short-chained cross-linking agents (such as glutaraldehyde) are used to form the oil-derived biomaterials and thus the adhesion barrier of the invention. It has been previously demonstrated in the literature that short chain cross-linking agents can elute during hydrolysis of biodegradable polymers and cause local tissue inflammation. The process of creating oil-derived biomaterials does not involve cross-linking agents because the oil is cured into a coating using oil autoxidation or photo-oxidation chemistry. The oxidation process results in the formation of carboxyl and hydroxyl functional groups that allow for the oil-derived biomaterial to become hydrated very rapidly and become slippery, which allows for frictional injury during and after implantation to be significantly reduced and/or eliminated. The methods of making the oil-derived biomaterials described in embodiments of the present invention allow the alkyl chains of the fatty acid, glyceride and other lipid byproducts present in the coating to be disordered, which creates a coating that is flexible and aids in handling of the material while being implanted.

There are several individual chemical components of the present inventive materials that aid in biocompatibility and the low to non-inflammatory response observed in-vivo. One aspect of exemplary embodiments of the present invention is that the process of creating an oil-derived biomaterial used to form the adhesion barrier as described herein results in low to non-detectable amounts of oxidized lipid byproducts of biocompatibility concern, such as aldehydes. These products are either almost completely reacted or volatilized during the curing process as described in exemplary embodiments of the present invention. The process of creating an oil-derived biomaterial largely preserves the esters of the native oil triglycerides and forms ester and/or lactone cross-links, which are biocompatible (K. Park et al., 1993; J. M. Andersen, 1995).

In addition to general chemical properties of an oil-derived biomaterial that assists in its biocompatibility, there are also specific chemical components that have positive biological properties. Another aspect is that the fatty acid chemistry produced upon creation of an oil-derived biomaterial is similar to the fatty acid chemistry of tissue. Thus, as fatty acids are eluting from the adhesion barrier they are not viewed as being "foreign" by the body and do not cause an inflammatory response. In fact, C14 (myristic) and C16 (palmitic) fatty acids present in the adhesion barrier have been shown in the literature to reduce production of α-TNF, an inflammatory cytokine. The expression of α-TNF has been identified as one of the key cytokines responsible for "turning on" inflammation in the peritoneal cavity after hernia repair, which can then lead to abnormal healing and adhesion formation (Y. C. Cheong et. al., 2001). α-TNF is also an important cytokine in vascular injury and inflammation (D. E. Drachman and D. I. Simon, 2005; S. E. Goldblum, 1989), such as vascular injury caused during a stent deployment. In addition to the fatty acids just specified, there have also been additional oxidized fatty acids identified that have anti-inflammatory properties. Another component identified from the fatty acid-derived biomaterials as described herein are delta-lactones (i.e., 6-membered ring cyclic esters). Delta-lactones have been identified as having anti-tumor properties (H. Tanaka et. al. *Life Sciences* 2007; Vol. 80, pgs 1851-1855).

The components identified herein are not meant to be limiting in scope to the present invention, as changes in starting oil composition and/or process conditions can invariably alter the fatty acid and/or oxidative byproduct profiles and can be tailored as needed depending on the intended purpose and site of application of the fatty acid-derived biomaterial.

In summary, the biocompatibility and observed in-vivo performance of fatty acid-derived biomaterials that form the adhesion barrier described herein are due to the elution of fatty acids during hydrolysis of the material during implantation and healing and are not only beneficial as to prevent a foreign body response in-vivo due to the similarity of the fatty acid composition of the material to native tissue (i.e., a biological "stealth" coating), but the specific fatty acids and/or other lipid oxidation components eluting from the coating aid in preventing foreign body reactions and reducing or eliminating inflammation, which leads to improved patient outcomes. Additionally, the fatty acid and glyceride components eluted from the fatty acid-derived biomaterial forming the fatty acid-based film of the adhesion barrier are able to be absorbed by local tissue and metabolized by cells, in, for example, the Citric Acid Cycle (M. J. Campell, "Biochemistry: Second Edition." 1995, pgs 366-389). Hence, the fatty acid-derived biomaterial described in accordance with the present invention is also bioabsorbable.

Methods of Treatment Using the Adhesion Barrier

In general, four types of soft tissue are present in humans: epithelial tissue, e.g., the skin and the lining of the vessels and many organs; connective tissue, e.g., tendons, ligaments, cartilage, fat, blood vessels, and bone; muscle, e.g., skeletal (striated), cardiac, or smooth; and nervous tissue, e.g., brain, spinal cord and nerves. The adhesion barrier in accordance with the present invention can be used to treat injury to these soft tissue areas. Thus, in one embodiment, the adhesion barrier of the present invention can be used for promotion of proliferation of soft tissue for wound healing. Furthermore, following acute trauma, soft tissue can undergo changes and adaptations as a result of healing and the rehabilitative process. Such changes include, but are not limited to, metaplasia, which is conversion of one kind of tissue into a form that is not normal for that tissue; dysplasia, with is the abnormal development of tissue; hyperplasia, which is excessive proliferation of normal cells in the normal tissue arrangement; and atrophy, which is a decrease in the size of tissue due to cell death and resorption or decreased cell proliferation. Accordingly, the fatty acid-derived biomaterial of the present invention can be used for the diminishment or alleviation of at least one symptom associated with or caused by acute trauma in soft tissue.

In accordance with one exemplary embodiment of the present invention, as described below, the adhesion barrier can be used to prevent tissue adhesion. The tissue adhesion can be, for example, a result of blunt dissection. Blunt dissection can be generally described as dissection accomplished by separating tissues along natural cleavage lines without cutting. Blunt dissection is executed using a number of different blunt surgical tools, as is understood by those of ordinary skill in the art. Blunt dissection is often performed in cardiovascular, colo-rectal, urology, gynecology, upper GI, and plastic surgery applications, among others.

After the blunt dissection separates the desired tissues into separate areas, there is often a need to maintain the separation of those tissues. In fact, post surgical adhesions can occur following almost any type of surgery, resulting in serious postoperative complications. The formation of surgical adhesions is a complex inflammatory process in which tissues that normally remain separated in the body come into physical contact with one another and attach to each other as a result of surgical trauma.

It is believed that adhesions are formed when bleeding and leakage of plasma proteins from damaged tissue deposit in the abdominal cavity and form what is called a fibrinous exudate. Fibrin, which restores injured tissues, is sticky, so the fibrinous exudate may attach to adjacent anatomical structures in the abdomen. Post-traumatic or continuous inflammation exaggerates this process, as fibrin deposition is a uniform host response to local inflammation. This attachment seems to be reversible during the first few days after injury because the fibrinous exudates go through enzymatic degradation caused by the release of fibrinolytic factors, most notably tissue-type plasminogen activator (t-PA). There is constant play between t-PA and plasminogen-activator inhibitors. Surgical trauma usually decreases t-PA activity and increases plasminogen-activator inhibitors. When this happens, the fibrin in the fibrinous exudate is replaced by collagen. Blood vessels begin to form, which leads to the development of an adhesion. Once this has occurred, the adhesion is believed to be irreversible. Therefore, the balance between fibrin deposition and degradation during the first few days post-trauma is critical to the development of adhesions (Holmdahl L. *Lancet* 1999; 353: 1456-57). If normal fibrinolytic activity can be maintained or quickly restored, fibrous deposits are lysed and permanent adhesions can be avoided. Adhesions can appear as thin sheets of tissue or as thick fibrous bands.

Often, the inflammatory response is also triggered by a foreign substance in vivo, such as an implanted medical device. The body sees this implant as a foreign substance, and the inflammatory response is a cellular reaction to wall off the foreign material. This inflammation can lead to adhesion formation to the implanted device; therefore a material that causes little to no inflammatory response is desired.

Thus, adhesion barrier of the present invention may be used as a barrier to keep tissues separated to avoid the formation of adhesions, e.g., surgical adhesions. Application examples for adhesion prevention include abdominal surgeries, spinal repair, orthopedic surgeries, tendon and ligament repairs, gynecological and pelvic surgeries, and nerve repair applications. The adhesion barrier may be applied over the trauma site or wrapped around the tissue or organ to limit adhesion formation. The addition of therapeutic agents to the fatty acid-derived biomaterial used in these adhesion prevention applications can be utilized for additional beneficial effects, such as pain relief or infection minimization. Other surgical applications of adhesion barrier may include using a stand-alone film as a dura patch, buttressing material, internal wound care (such as a graft anastomotic site), and internal drug delivery system. The adhesion barrier may also be used in applications in transdermal, wound healing, and non-surgical fields. The adhesion barrier may be used in external wound care, such as a treatment for burns or skin ulcers. The adhesion barrier may be used without any therapeutic agent as a clean, non-permeable, non-adhesive, non-inflammatory, anti-inflammatory dressing, or the adhesion barrier may be used with one or more therapeutic agents for additional beneficial effects. The adhesion barrier may also be used as a transdermal drug delivery patch when the fatty acid-derived biomaterial is loaded or coated with one or more therapeutic agents.

The process of wound healing involves tissue repair in response to injury and it encompasses many different biologic processes, including epithelial growth and differentiation, fibrous tissue production and function, angiogenesis, and inflammation. Accordingly, the adhesion barrier provides an excellent material suitable for wound healing applications.

Combining fatty acid-based films with tissue fixating materials results in an effective adhesion barrier with fixating and anti-inflammation properties. The resulting adhesion barrier is well-tolerated by the body, reduces adhesions post-surgery, and does not migrate from the target site due to the film's fixating properties. Further, the adhesion barrier is absorbed into the body relatively slowly as compared to conventional CMC-based films, and so facilitates tissue adhesion between the adhesion barrier and the site of treatment for up to 28 days. This provides sufficient residence time to effectively provide post-surgery barrier functionality. Further, combining fatty acid-based films with tissue fixating materials may avoid the need to crosslink the tissue fixating material, reducing the cost and complexity of manufacturing the film.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure can vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations and web pages, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The section headings used herein are for organizational purposes only and are not to be construed as limiting the subject matter described in any way.

While the present inventions have been described in conjunction with various embodiments and examples, it is not intended that the present teachings be limited to such embodiments or examples. On the contrary, the present inventions encompass various alternatives, modifications, and equivalents, as will be appreciated by those of skill in the art.

The claims should not be read as limited to the described order or elements unless stated to that effect. It should be understood that various changes in form and detail can be made without departing from the scope of the appended claims. Therefore, all embodiments that come within the scope and spirit of the following claims and equivalents thereto are claimed.

The invention claimed is:

1. An adhesion barrier comprising:
   an anti-adhesion material forming the adhesion barrier, wherein the anti-adhesion material has tissue anti-adhesion characteristics and the anti-adhesion material comprises omega-3 fatty acids cross-linked directly to each other, wherein the cross-links include ester bonds, wherein the anti-adhesion material is the product of cross-linking an oil composition that includes eicosapentaenoic acid, docosahexanoic acid and alpha-linolenic acid, wherein the oil composition is obtained from fish oil and the fish oil is cured to form a material from which cured fish oil particles having a distribution of size about 1-12 μm (v, 0.1), 21-40 μm (v, 0.5), and 41-150 μm (v, 0.9) are obtained, wherein the anti-adhesion material is bioabsorbable, and wherein the anti-adhesion material is formulated as an emulsion that is a dispersion of the cured fish oil particles in fish oil mixed with an emulsion base, wherein the emulsion base comprises carboxymethyl cellulose and water.

2. The adhesion barrier of claim 1, wherein the cured fish oil particles have a mean particle size in the range of about 1 micron to about 50 microns.

3. The adhesion barrier of claim 1, wherein the anti-adhesion material forms a layer.

4. The adhesion barrier of claim 1, wherein the cured fish oil particles are associated with a therapeutic agent.

* * * * *